(12) United States Patent
Nagasaki et al.

(10) Patent No.: US 7,993,874 B2
(45) Date of Patent: Aug. 9, 2011

(54) PHOSPHOLIPASE C ENZYME(S)

(75) Inventors: Eiko Nagasaki, Tokyo (JP); Tetsuya Fukazawa, Yokohama (JP); Yasunori Ono, Tokyo (JP)

(73) Assignee: Mitsubishi-Kagaku Foods Corporation, Tokyo (JP)

( * ) Notice: Subject to any disclaimer, the term of this patent is extended or adjusted under 35 U.S.C. 154(b) by 49 days.

(21) Appl. No.: 12/224,867

(22) PCT Filed: Mar. 10, 2006

(86) PCT No.: PCT/JP2006/304710
§ 371 (c)(1),
(2), (4) Date: Sep. 8, 2008

(87) PCT Pub. No.: WO2007/105264
PCT Pub. Date: Sep. 20, 2007

(65) Prior Publication Data
US 2009/0053768 A1    Feb. 26, 2009

(51) Int. Cl.
*C12P 21/06*    (2006.01)
(52) U.S. Cl. ......... 435/69.1; 435/7.1; 435/6; 435/320.1; 435/325; 530/350
(58) Field of Classification Search ...................... None
See application file for complete search history.

(56) References Cited

U.S. PATENT DOCUMENTS
2010/0166761 A1*  7/2010  Bodary-Winter et al. . 424/139.1

FOREIGN PATENT DOCUMENTS
| JP | 49-55893 | 5/1974 |
| JP | 50-107183 | 8/1975 |
| JP | 2000-166543 A | 6/2000 |
| JP | 2004-502430 A | 1/2004 |
| JP | 2005-328781 A | 12/2005 |
| WO | WO 02/02791 A | 1/2002 |
| WO | WO 2004/104193 A2 | 12/2004 |

OTHER PUBLICATIONS

Tuddenham et al. (Nucleic Acids Research, vol. 22, No. 17, pp. 3511-3533, 1994).*
Sunee Korbsrisate et al., "Cloning and Characterization of a Nonhemolytic Phospholipase C Gene from *Burkholderia pseudomallei*," *Journal of Clinical Microbiology*, 1999, vol. 37, pp. 3742-3745.
Cristina A. Tan et al., "Cloning, Overexpression, Refolding, and Purification of the Nonspecific Phospholipase C from *Bacillus cereus*," *Protein Expression and Purification*, 1997, vol. 10, pp. 365-372.
Shannon Daugherty et al., "Cloning, Expression, and Mutagenesis of Phosphatidylinositol-Specific Phospholipase C from *Staphylococcus aureus*: a Potential Staphylococcal Virulence Factor," *Infection and Immunity*, 1993, vol. 61, pp. 5078-5089.
Richard W. Titball et al., "Molecular Cloning and Nucleotide Sequence of the Alpha-Toxin (Phospholipase C) of *Clostridium perfringens*," *Infection and Immunology*, 1989, vol. 57, pp. 367-376.

Encarmación Andaluz et al., "Sequencing of a 4.3 kbp region of chromosome 2 of *Candida albicans* reveals the presence of homologues of SHE9 from *Saccharomyces cerevisiae* and of bacterial phosphatidylinositol-phospholipase C," *Yeast*, 2001, vol. 18, pp. 711-721.
William E. Payne et al., "A Mutation in *PLC1*, a Candidate Phosphoinositide-Specific Phospholipase C Gene from *Saccharomyces cerevisiae*, Causes Aberrant Mitotic Chromosome Segregation," *Molecular and Cellular Biology*, 1993, vol. 13, pp. 4351-4364.
Shigeru Matsuoka et al., "Purification and Properties of a Phospholipase C That Has High Activity toward Sphingomyelin from *Aspergillus saitoi*," *Biotechnology and Applied Biochemistry*, 1987, vol. 9, pp. 401-409.
English-language International Preliminary Report on Patentability and Written Opinion of the International Searching Authority, dated Sep. 25, 2008 for International Application PCT/JP2006/304710 filed Mar. 10, 2006; Applicants: Mitsubishi-Kagaku Foods Corporation et al.
JCM Catalogue, RIKEN BioResource Center; 2004, Database accession No. IAM13907.
Song J.K. et al., "Phospholipases: Occurrence and Production in Microorganisms, Assay for High-Throughput Screening, and Gene Discovery from Natural and Man-Made Diversity" *Journal of the Americal Oil Chemists Society*, 2005, Springer Verlag US, vol. 82, No. 10, pp. 691-705.
Database EMBL [Online] Jun. 18, 2004, EST836500, "*Aspergillus flavus* Normalized cDNA Expression Library *Aspergillus flavus* cDNA clone NAFEH30 5' end, mRNA sequence," retrived from EBI accession No. EMBL: C0141829.
Supplementary European Search Report dated Feb. 16, 2010 for EP 0 672 878.
S. Matsuoka et al., "Purification and Properties of a Phospholipase C That has High Activity toward Sphingomyelin from *Aspergillus saitoi*," *Biotechnology and Applied Biochem.*, 1987, vol. 9, No. 5, pp. 401 to 409.
M. Birch et al., "Evidence of Multiple Extracellular Phospholipase Activities of *Aspergillus fumigatus*," *Infect. Immun.*, 1996, vol. 64, No. 3, pp. 751 to 755.
Japanese Office Action dated Jun. 22, 2010, which issued in the counterpart Japanese Patent Application No. 2005--38929, and an English-language translation thereof.
Chinese Office Action dated Apr. 30, 2010, which issued in the counterpart Chinese Patent Application No. 200680053785.2 and an English-language translation thereof.
EMBL registration No. AP 007157.1, Dec. 23, 2005.
Japanese Office Action dated Oct. 5, 2010, which issued in the counterpart Japanese Patent Application No. 2005-037829.
Oyashiki et al., "Screening for Strains of *Aspergillus oryzae* That Degrade Carbamide for Use in Sake Brewing," *Journal of Fermentation and Bioengineering*, vol. 71, No. 2, 126-127, 1991.

* cited by examiner

*Primary Examiner* — Hope Robinson
(74) *Attorney, Agent, or Firm* — Holtz, Holtz, Goodman & Chick P C

(57) ABSTRACT

The present invention provides a phospholipase C enzyme(s) having ability to hydrolyze phospholipid in both acidic and around neutral ranges and the activity in a citrate buffer solution as well as having some degree of heat stability, and having a property not to hydrolyze phosphate esters not containing lipid moieties. The phospholipase C enzyme(s) shows the activity at from acidic to neutral pH and does not substantially hydrolyze any phosphate esters except for phospholipids.

3 Claims, 9 Drawing Sheets

SEQUENCE LISTING

<160> NUMBER OF SEQ ID NOS: 9

<210> SEQ ID NO 1
<211> LENGTH: 15
<212> TYPE: PRT
<213> ORGANISM: Aspergillus oryzae

<400> SEQUENCE: 1

Thr Ala Asp Ser Ala Thr Ala Ile Gly Tyr Val Thr Pro Ser Met
1               5                   10                  15

<210> SEQ ID NO 2
<211> LENGTH: 10
<212> TYPE: PRT
<213> ORGANISM: Aspergillus oryzae

<400> SEQUENCE: 2

Glu Ala Tyr Gly Ser Leu Leu Thr Pro Pro
1               5                   10

<210> SEQ ID NO 3
<211> LENGTH: 10
<212> TYPE: PRT
<213> ORGANISM: Aspergillus oryzae

<400> SEQUENCE: 3

Val Pro Pro Ser His Asn Pro Gln Trp Ala
1               5                   10

<210> SEQ ID NO 4
<211> LENGTH: 2085
<212> TYPE: DNA
<213> ORGANISM: Aspergillus oryzae
<220> FEATURE:
<221> NAME/KEY: CDS
<222> LOCATION: (46)..(1899)
<223> OTHER INFORMATION:

<400> SEQUENCE: 4

```
gctgcagctt ggtcagcgat cttgacctcg tatcaaacta gggac atg aga cca gct      57
                                                 Met Arg Pro Ala
                                                   1 ttc ttc ctt gcg gcc ctg gcc tcc ctg gct agt act cat gct aat cct       105
Phe Phe Leu Ala Ala Leu Ala Ser Leu Ala Ser Thr His Ala Asn Pro
  5                  10                  15                  20 gag gcc gac ttg gct ggc tcg atc tgg gat gat ttc aaa gga gca gtc       153
Glu Ala Asp Leu Ala Gly Ser Ile Trp Asp Asp Phe Lys Gly Ala Val
                 25                  30                  35 acc tgt gct ggc tgt gag ggc ctg ctc ggg gca ctc aaa cta gta gcc       201
Thr Cys Ala Gly Cys Glu Gly Leu Leu Gly Ala Leu Lys Leu Val Ala
             40                  45                  50 ggt ctg ggt caa agt gca ttg gaa cat gtt gtg acc gac gcg tgt acg       249
Gly Leu Gly Gln Ser Ala Leu Glu His Val Val Thr Asp Ala Cys Thr
         55                  60                  65 ttg gca ggg atc gag gat gac gat gtc tgt gag ggc gca atc aaa gaa       297
Leu Ala Gly Ile Glu Asp Asp Asp Val Cys Glu Gly Ala Ile Lys Glu
     70                  75                  80 gaa ggc gcg gcc gtg tat tac gcc ctg aag aat ctg aag gtc ggc tcg       345
Glu Gly Ala Ala Val Tyr Tyr Ala Leu Lys Asn Leu Lys Val Gly Ser
 85                  90                  95                 100 cat aca tcc aaa act ttc tgc tca agt att gcc ggc ctg tgc gat tac       393
His Thr Ser Lys Thr Phe Cys Ser Ser Ile Ala Gly Leu Cys Asp Tyr
                105                 110                 115 cct gac gtt cgg cca tac aac ctc aca ttc ccc gta gcc aag tcc tcg       441
Pro Asp Val Arg Pro Tyr Asn Leu Thr Phe Pro Val Ala Lys Ser Ser
            120                 125                 130 gtc act cgt cca ccc ccg agt ggc cag tct ccg atc cgt gtc gca cac       489
Val Thr Arg Pro Pro Pro Ser Gly Gln Ser Pro Ile Arg Val Ala His
        135                 140                 145
```

```
att agt gac acg cac gtt gat ttg cag tac acc ccc gga gcc aat gca    537
Ile Ser Asp Thr His Val Asp Leu Gln Tyr Thr Pro Gly Ala Asn Ala
    150                 155                 160 caa tgc acc aag cct att tgc tgt cgt agt ttc acc ccg gaa gac gcc    585
Gln Cys Thr Lys Pro Ile Cys Cys Arg Ser Phe Thr Pro Glu Asp Ala
165                 170                 175                 180 ccc ggt aac gcc tca agc ccc tgc ggg ctc tgg ggt gac cat cac tgt    633
Pro Gly Asn Ala Ser Ser Pro Cys Gly Leu Trp Gly Asp His His Cys
                    185                 190                 195 gat cct cca ctt cgt ctc gag gac tcc atg atg gac gct atc gcg gcc    681
Asp Pro Pro Leu Arg Leu Glu Asp Ser Met Met Asp Ala Ile Ala Ala
                200                 205                 210 ctc aat cca acg ttc tcc atc tat acg ggt gac gtt ccc cca cac gac    729
Leu Asn Pro Thr Phe Ser Ile Tyr Thr Gly Asp Val Pro Pro His Asp
            215                 220                 225 atc tgg ctt gtg aac cag agc tca gtc ctg cag agc ttc aac tcc acc    777
Ile Trp Leu Val Asn Gln Ser Ser Val Leu Gln Ser Phe Asn Ser Thr
        230                 235                 240 tac tcc aac ctg ggg aaa ctg ggc gtc gtc tac gcg gcc ttg gga aat    825
Tyr Ser Asn Leu Gly Lys Leu Gly Val Val Tyr Ala Ala Leu Gly Asn
245                 250                 255                 260 cac gac gca gcc cca gtc aac ctc ttc cct tcg gac aaa gtc ccg ccc    873
His Asp Ala Ala Pro Val Asn Leu Phe Pro Ser Asp Lys Val Pro Pro
                    265                 270                 275 tct cac aac ccc caa tgg gcc tac gat gcc ctg gcc agc gac tgg tcc    921
Ser His Asn Pro Gln Trp Ala Tyr Asp Ala Leu Ala Ser Asp Trp Ser
                280                 285                 290 aac ctc gtc gag ggt tca cct agc tca act acc aaa cac ggt tcc tac    969
Asn Leu Val Glu Gly Ser Pro Ser Ser Thr Thr Lys His Gly Ser Tyr
            295                 300                 305 tcc atc atc cac ccc aat tcc aac ctc cgc atc atc tcc tac aac agc    1017
Ser Ile Ile His Pro Asn Ser Asn Leu Arg Ile Ile Ser Tyr Asn Ser
        310                 315                 320 gtc ttc tac tac aaa tac aac ttc tac gca ttc cag gaa cca atg gaa    1065
Val Phe Tyr Tyr Lys Tyr Asn Phe Tyr Ala Phe Gln Glu Pro Met Glu
325                 330                 335                 340 tac gac ccg gac aac caa ctc cac tgg ctc atc tcc gag ctg caa gcc    1113
Tyr Asp Pro Asp Asn Gln Leu His Trp Leu Ile Ser Glu Leu Gln Ala
                    345                 350                 355 gcc gag acc gcc ggc cag cgc gtc tgg atg atc gct cac atc ccc acc    1161
Ala Glu Thr Ala Gly Gln Arg Val Trp Met Ile Ala His Ile Pro Thr
                360                 365                 370 ggc aac acc gac acc ctg cac gac tac tca cac tac ctc gat cag atc    1209
Gly Asn Thr Asp Thr Leu His Asp Tyr Ser His Tyr Leu Asp Gln Ile
            375                 380                 385 atc aac cgc tac agc gcc agc atc gcc gcc ctc ttc ttc ggc cac act    1257
Ile Asn Arg Tyr Ser Ala Ser Ile Ala Ala Leu Phe Phe Gly His Thr
        390                 395                 400 cac act gac ctc ttc caa att tcg tac acc aac tac acc gcc cgc acc    1305
His Thr Asp Leu Phe Gln Ile Ser Tyr Thr Asn Tyr Thr Ala Arg Thr
405                 410                 415                 420 gcc gac tct gcc acc gca atc ggc tac gtc acc cca tcc atg acc ccg    1353
Ala Asp Ser Ala Thr Ala Ile Gly Tyr Val Thr Pro Ser Met Thr Pro
                    425                 430                 435 gac tcg ggc gcc cca gcc ttc cgc atc tac gac att gac ccc gtc acc    1401
Asp Ser Gly Ala Pro Ala Phe Arg Ile Tyr Asp Ile Asp Pro Val Thr
                440                 445                 450 ttc gct gtg ctc gac tac act gtc tac acg gcc gac atc aac agc acc    1449
Phe Ala Val Leu Asp Tyr Thr Val Tyr Thr Ala Asp Ile Asn Ser Thr
            455                 460                 465
```

```
gat tcc ccc aac acc cca cct aaa tgg gtc aaa tac tac tcc gcc aaa    1497
Asp Ser Pro Asn Thr Pro Pro Lys Trp Val Lys Tyr Tyr Ser Ala Lys
        470                 475                 480 gaa gcc tac ggc tcc ctt ctg acc cca ccc gtc acc gac ccc aat gtt    1545
Glu Ala Tyr Gly Ser Leu Leu Thr Pro Pro Val Thr Asp Pro Asn Val
485                 490                 495                 500 gaa atg acc ccc tcc ttc tgg cac aag gtc aca gcc caa atg gag aag    1593
Glu Met Thr Pro Ser Phe Trp His Lys Val Thr Ala Gln Met Glu Lys
                505                 510                 515 gat gac tcc gtc ttc cag gcg tgg tgg tcg cgc acc acg aga ggt tac    1641
Asp Asp Ser Val Phe Gln Ala Trp Trp Ser Arg Thr Thr Arg Gly Tyr
        520                 525                 530 aat gtc acg gag tgc acg ggg gag tgt gca aag aat aag att tgc tcc    1689
Asn Val Thr Glu Cys Thr Gly Glu Cys Ala Lys Asn Lys Ile Cys Ser
                535                 540                 545 ctg cgc ggc gga gac gca cag ttc aac tgc gag ggt ccg ggg acg ccg    1737
Leu Arg Gly Gly Asp Ala Gln Phe Asn Cys Glu Gly Pro Gly Thr Pro
        550                 555                 560 ttt agt att acg aag cgg agt gat ggt gta aac gag gtg cat gtg gag    1785
Phe Ser Ile Thr Lys Arg Ser Asp Gly Val Asn Glu Val His Val Glu
565                 570                 575                 580 agg ccc ttc tgt gag gat gca gtg ttg gcg agg att gtc ggg ggg ttg    1833
Arg Pro Phe Cys Glu Asp Ala Val Leu Ala Arg Ile Val Gly Gly Leu
                585                 590                 595 gcg cgg aag ggt gtc gat gcg gaa aag ttt gtt cgg gag aag gcg aag    1881
Ala Arg Lys Gly Val Asp Ala Glu Lys Phe Val Arg Glu Lys Ala Lys
        600                 605                 610 ctt tat gag aag gct taa gttgactggg gaaggattca atctctgtga           1929
Leu Tyr Glu Lys Ala
                615 cgttgttgat atcttgtctt ggtatatata atgttgagtg tctaatgatc caccttcgga  1989 aacattaact ttaggactct ctttagaaag gatctactta tgccacggca taggatccgg  2049 agtatatagc gagaaagaaa ccaagcgtga cctgat                            2085

<210> SEQ ID NO 5
<211> LENGTH: 617
<212> TYPE: PRT
<213> ORGANISM: Aspergillus oryzae

<400> SEQUENCE: 5

Met Arg Pro Ala Phe Phe Leu Ala Ala Leu Ala Ser Leu Ala Ser Thr
1               5                   10                  15

His Ala Asn Pro Glu Ala Asp Leu Ala Gly Ser Ile Trp Asp Asp Phe
                20                  25                  30

Lys Gly Ala Val Thr Cys Ala Gly Cys Glu Gly Leu Leu Gly Ala Leu
            35                  40                  45

Lys Leu Val Ala Gly Leu Gly Gln Ser Ala Leu Glu His Val Val Thr
        50                  55                  60

Asp Ala Cys Thr Leu Ala Gly Ile Glu Asp Asp Val Cys Glu Gly
65                  70                  75                  80

Ala Ile Lys Glu Glu Gly Ala Ala Val Tyr Tyr Ala Leu Lys Asn Leu
                85                  90                  95

Lys Val Gly Ser His Thr Ser Lys Thr Phe Cys Ser Ser Ile Ala Gly
            100                 105                 110

Leu Cys Asp Tyr Pro Asp Val Arg Pro Tyr Asn Leu Thr Phe Pro Val
        115                 120                 125

Ala Lys Ser Ser Val Thr Arg Pro Pro Ser Gly Gln Ser Pro Ile
    130                 135                 140
```

-continued

```
Arg Val Ala His Ile Ser Asp Thr His Val Asp Leu Gln Tyr Thr Pro
145                 150                 155                 160

Gly Ala Asn Ala Gln Cys Thr Lys Pro Ile Cys Cys Arg Ser Phe Thr
            165                 170                 175

Pro Glu Asp Ala Pro Gly Asn Ala Ser Ser Pro Cys Gly Leu Trp Gly
        180                 185                 190

Asp His His Cys Asp Pro Pro Leu Arg Leu Glu Asp Ser Met Met Asp
        195                 200                 205

Ala Ile Ala Ala Leu Asn Pro Thr Phe Ser Ile Tyr Thr Gly Asp Val
        210                 215                 220

Pro Pro His Asp Ile Trp Leu Val Asn Gln Ser Ser Val Leu Gln Ser
225                 230                 235                 240

Phe Asn Ser Thr Tyr Ser Asn Leu Gly Lys Leu Gly Val Val Tyr Ala
                245                 250                 255

Ala Leu Gly Asn His Asp Ala Ala Pro Val Asn Leu Phe Pro Ser Asp
            260                 265                 270

Lys Val Pro Pro Ser His Asn Pro Gln Trp Ala Tyr Asp Ala Leu Ala
        275                 280                 285

Ser Asp Trp Ser Asn Leu Val Glu Gly Ser Pro Ser Ser Thr Thr Lys
        290                 295                 300

His Gly Ser Tyr Ser Ile Ile His Pro Asn Ser Asn Leu Arg Ile Ile
305                 310                 315                 320

Ser Tyr Asn Ser Val Phe Tyr Tyr Lys Tyr Asn Phe Tyr Ala Phe Gln
                325                 330                 335

Glu Pro Met Glu Tyr Asp Pro Asp Asn Gln Leu His Trp Leu Ile Ser
            340                 345                 350

Glu Leu Gln Ala Ala Glu Thr Ala Gly Gln Arg Val Trp Met Ile Ala
        355                 360                 365

His Ile Pro Thr Gly Asn Thr Asp Thr Leu His Asp Tyr Ser His Tyr
        370                 375                 380

Leu Asp Gln Ile Ile Asn Arg Tyr Ser Ala Ser Ile Ala Ala Leu Phe
385                 390                 395                 400

Phe Gly His Thr His Thr Asp Leu Phe Gln Ile Ser Tyr Thr Asn Tyr
                405                 410                 415

Thr Ala Arg Thr Ala Asp Ser Ala Thr Ala Ile Gly Tyr Val Thr Pro
            420                 425                 430

Ser Met Thr Pro Asp Ser Gly Ala Pro Ala Phe Arg Ile Tyr Asp Ile
        435                 440                 445

Asp Pro Val Thr Phe Ala Val Leu Asp Tyr Thr Val Tyr Thr Ala Asp
        450                 455                 460

Ile Asn Ser Thr Asp Ser Pro Asn Thr Pro Pro Lys Trp Val Lys Tyr
465                 470                 475                 480

Tyr Ser Ala Lys Glu Ala Tyr Gly Ser Leu Leu Thr Pro Pro Val Thr
                485                 490                 495

Asp Pro Asn Val Glu Met Thr Pro Ser Phe Trp His Lys Val Thr Ala
            500                 505                 510

Gln Met Glu Lys Asp Asp Ser Val Phe Gln Ala Trp Trp Ser Arg Thr
        515                 520                 525

Thr Arg Gly Tyr Asn Val Thr Glu Cys Thr Gly Glu Cys Ala Lys Asn
        530                 535                 540

Lys Ile Cys Ser Leu Arg Gly Asp Ala Gln Phe Asn Cys Glu Gly
545                 550                 555                 560

Pro Gly Thr Pro Phe Ser Ile Thr Lys Arg Ser Asp Gly Val Asn Glu
```

```
                        565                 570                 575
Val His Val Glu Arg Pro Phe Cys Glu Asp Ala Val Leu Ala Arg Ile
            580                 585                 590

Val Gly Gly Leu Ala Arg Lys Gly Val Asp Ala Glu Lys Phe Val Arg
        595                 600                 605

Glu Lys Ala Lys Leu Tyr Glu Lys Ala
    610                 615

<210> SEQ ID NO 6
<211> LENGTH: 20
<212> TYPE: DNA
<213> ORGANISM: Artificial
<220> FEATURE:
<223> OTHER INFORMATION: Primer Sequence for Aspergillus oryzae

<400> SEQUENCE: 6
ggccacgcgt cgactagtac                                                   20

<210> SEQ ID NO 7
<211> LENGTH: 24
<212> TYPE: DNA
<213> ORGANISM: Artificial
<220> FEATURE:
<223> OTHER INFORMATION: Primer Sequence for Aspergillus oryzae

<400> SEQUENCE: 7
gacagtgtag tcgagcacag cgaa                                              24

<210> SEQ ID NO 8
<211> LENGTH: 23
<212> TYPE: DNA
<213> ORGANISM: Artificial
<220> FEATURE:
<223> OTHER INFORMATION: Primer Sequence for Aspergillus oryzae

<400> SEQUENCE: 8
gactctgcca ccgcaatcgg cta                                               23

<210> SEQ ID NO 9
<211> LENGTH: 20
<212> TYPE: DNA
<213> ORGANISM: Artificial
<220> FEATURE:
<223> OTHER INFORMATION: Primer Sequence for Aspergillus oryzae

<400> SEQUENCE: 9
ggccacgcgt cgactagtac                                                   20
```

PHOSPHOLIPASE C ENZYME(S)

CROSS-REFERENCE TO RELATED APPLICATION

This application is the United States national phase application of International Application PCT/JP2006/304710 filed Mar. 10, 2006.

TECHNICAL FIELD

The present invention relates to a phospholipase C enzyme(s), filamentous fungi producing the phospholipase C enzyme(s), a method for separating/purifying the phospholipase C enzyme(s) from the cultured products of filamentous fungi, DNA encoding the phospholipase C enzyme(s), a method for producing the phospholipase C enzyme(s) and so forth. Specifically, the present invention relates to the phospholipase C enzyme(s), particularly suitable for the use in food and pharmaceutical industries, the phospholipase C enzyme(s) produced particularly by filamentous fungi, *Aspergillus oryzae* or *Aspergillus tamarii*, filamentous fungi producing the phospholipase C enzyme(s), a method for separating/purifying the phospholipase C enzyme(s) from the culture products of filamentous fungi, DNA encoding the phospholipase C enzyme(s), a method for producing the phospholipase C enzyme(s), and so forth.

BACKGROUND ART

[1] Phospholipase C Enzyme(s)

Conventionally, it is known that animals and microorganisms produce phospholipase C enzyme(s). The major animal-derived enzymes are phosphatidylinositol-selective phospholipase C enzymes. Among microorganism-derived enzymes, phospholipase C enzymes derived from bacteria, actinomycetes, yeast and fungi are known. The phospholipase C enzymes produced by bacteria, actinomycetes and yeast are almost phosphatidylinositol- or glycerophosphorylcholine-selective enzymes.

Known bacteria-derived phospholipase C enzymes include, for example, phospholipase C enzymes produced by *Pseudomonas schuylkilliensis* (See, for example, Patent Document 1: Japanese Patent Application Kokai Publication No. S50-1017183/1975), *Burkholderia pseudomallei* (See, for example, Nonpatent Document 1: Korbsrisate S. et al., Journal of Clinical Microbiology, 1999, Vol. 37, p. 3742-3745), *Bacillus cereus* (See, for example, Nonpatent Document 2: Tan C. et al., Protein Expression and Purification, 1997, Vol. 10, p 365-372), *Staphylococcus aureus* (See, for example, Nonpatent Document 3: Daugherty S. et al., Infection and Immunity, 1993, Vol. 61, p 5078-5089) and *Clostridium perfringens* (See, for example, Nonpatent Document 4: Titball R. et al., Infection and Immunity, 1989, Vol. 57, p 367-376).

Known actinomycetes-derived phospholipase C enzymes include, for example, phospholipase C enzymes produced by *Streptomyces hachijyoensis* (See, for example, Patent Document 2: Japanese Patent Application Kokai Publication No. S49-55893/1974).

Known yeast-derived phospholipase C enzymes include, for example, phospholipase C enzymes produced by *Candida albicans* (See, for example, Nonpatent Document 5: Andaluz E. et al., Yeast, 2001, Vol. 18, p 711-721) and *Saccharomyces cerevisiae* (See, for example, Nonpatent Document 6: Payne W. et al., Molecular and Cellular Biology, 1993, Vol. 13, p 4351-4364).

Conventionally, two fungi-derived phospholipase C enzymes are known. One is the phospholipase C produced by *Aspergillus niger* (See, for example, Patent Document 3: Japanese Patent Application Kokai Publication No. 2000-166543), and the other is one produced by *Aspergillus saitoi* (See, for example, Nonpatent Document 7: Matsuoka S. et al., Biotechnology and Applied Biochemistry, 1987, Vol. 9, p 401-409).

[2] Lecithin

Lecithin is a representative glycerophospholipid widely distributed among animals, plants and fungi. Glycerophospholipid is a compound having a phosphoryl base covalently bonding to the 3 position of 1,2-diacylglycerol. Choline, ethanolamine, serine, inositol, glycerol, etc. are included as bases, and the composition rate is different depending on sources. The word, lecithin, shall be used as a general idea included in glycerophospholipid.

Lecithin has a surfactant action, antioxidant action, physiological action, etc., and is used for foods, feeds, medicaments, etc. In food industry, the unartificial lecithins, typified by egg yolk lecithin, soybean lecithin, etc., are used as food additives, mainly to modify food properties as an emulsifier and the like, and is supplied abundantly.

[3] Enzyme Treatment of Lecithin

Partially hydrolyzing lecithin enzymatically to provide new properties has also been investigated. Enzymes used for this include phospholipases and phospholipases A, B, C and D are known. Phospholipase A hydrolyzes a fatty acid moiety selectively at the 1 or 2 position of glycerophospholipid. Phospholipase B hydrolyzes glycerophospholipid nonselectively; phospholipase C hydrolyzes glycerophospholipid into diacylglycerol and a phosphoryl base; and phospholipase D hydrolyzes glycerophospholipid into phosphatidic acid and a base.

In the field of food industry, phospholipase A is used comparatively most widely at present. Lecithin is poorly soluble in water and acting phospholipase A on lecithin results in hydrolyzing the acyl group partially to generate water-soluble lysolecithin. When lysolecithin is used as a food additive, the physical properties of the obtained foods may differ from those of foods conventionally obtained using lecithin.

[4] Sphingophospholipid

Sphingophospholipid is composed of phospholipid with glycerophospholipid.

Typical sphingophospholipid is sphingomyelin, a compound in which a choline phosphate is phosphodiester-bonding to the primary alcohol of ceramide. Sphingomyelin is contained in various internal organs of animals. Since sphingomyelin is contained also in breast milk, it may be blended into the powdered infant milk.

Phospholipase C enzyme(s) acts on sphingomyelin to remove a choline phosphate and generate ceramide. Ceramide is widely used in cosmetics as a moisturizing agent. Besides, it's been reported that atopic dermatitis is cause by ceramide deficiency.

[5] Use of Phospholipase C Enzyme(s) in Food

As indicated in the following figure, use of phospholipase C enzyme(s) can produce diacylglycerol from lecithin in the presence of water.

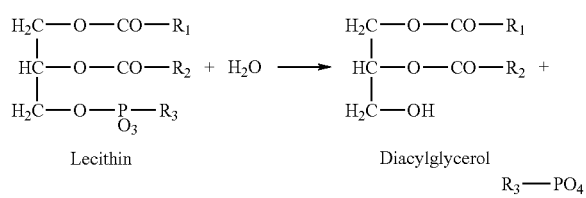

Lecithin → Diacylglycerol $R_3—PO_4$ (wherein each of $R_1$ and $R_2$ represents an alkyl group, and $R_3$ represents a group such as choline, ethanolamine, glycerol or inositol.)

By carrying out such reaction in food materials, it may be possible to supply products having different properties essentially from those obtained by acting phospholipase A.

The phospholipase C enzyme(s) used herein is required to hydrolyze various glycerophospholipids. For example, soybean lecithin is known to contain mainly phosphatidylcholine and phosphatidylethanolamine as well as phosphatidylglycerol or phosphatidylinositol, etc. Egg yolk lecithin contains mainly phosphatidylcholine and phosphatidylethanolamine. Therefore, it is desirable that the phospholipase C enzyme(s) used herein hydrolyzes these indiscriminately.

However, a large amount of phosphate in addition to phospholipid are contained in foods, and it is not preferable to hydrolyze them to liberate phosphoric acid, since this further deteriorates the properties of foods. Therefore, phospholipase C enzyme(s) that does not hydrolyze phosphate esters except for phospholipid, is desirable; and for example, phospholipase C enzyme(s), which has no enzymatic activity against phosphate esters such as glycerophosphorylcholine that are similar to phospholipid but do not have lipid moieties, is desirable.

From the same viewpoints, it is desirable that the phospholipase C enzyme(s) used is a protein not having phosphatase activity. That is, the phospholipase C enzyme(s) having no degradation activity of p-nitrophenylphosphate, a substrate of phosphatase, is desirable.

In food industry, it is preferable to carry out various treatments in from a neutral to weak acidic range to prevent deterioration of foods; it is desirable that an enzyme preparation containing phospholipase, etc., has high activity in this pH range.

[6] Use of Phospholipase C Enzyme(s) in Food Industry

The intended purposes of phospholipase C enzyme(s) includes, for example, mitigation of the surface aging and white spots like pear skin during baking frozen bread dough and improvement of purification process of edible oil.

Lecithin is a substance that should be removed, since it causes coloring or deterioration of flavor during manufacturing edible oil from soybean, rapeseed, etc. For this purpose, a method for removing lecithin by partially hydrolyzing lecithin using phospholipase A to lead to aqueous lysolecithin, has been conventionally investigated.

However, here, lecithin can be converted to diacylglycerol using phospholipase C enzyme(s), which is one component of the oil along with triacylglycerol. That is, the improving effect on yields can be expected in the manufacturing process of edible oil.

The phospholipase C enzymes used herein are required to hydrolyze various phospholipids. For example, the above various phospholipids are contained in soybean oils. Similarly, various phospholipids are contained also in cotton seed oils or rapeseed oils. It is desirable that the phospholipase C enzymes used herein hydrolyze these indiscriminately.

Since, in oil mills industries, impurities except for oils are removed under an acidic heating condition, use of an enzyme preparation of which activity is high in an acidic range and which has some degree of heat stability, is desired. Since citric acid may be used to acidify raw oils to be treated, the activity in the presence of citric acid and some degree of heat stability are required for the phospholipase C enzymes used herein.

[7] Problems of Known Phospholipase C Enzymes

The phospholipase C enzymes, produced by animals, bacteria, actinomycetes or yeast, are mainly phosphatidylinositol- or phosphatidylcholine-selective and therefore they are not suitable for use in the food industries in which degradation of various substrates is required. In addition, the enzyme preparation originated from animals cannot be accepted in some countries and areas for religious reasons, and there is also a problem of a wide usability. Furthermore, most bacteria that produce phospholipase C enzymes are pathogenic and therefore there are safety problems.

The phospholipase C enzymes derived from filamentous fungi and known conventionally, have a property to hydrolyze various phospholipids. Besides, any filamentous fungi, conventionally used for the production of phospholipase C enzymes, are characterized in having the actual results in the production of edible enzymes. The enzymes derived from both species of *Aspergillus niger* and *Aspergillus saitoi* have extremely similar properties regarding temperature or pH and the same molecular weight. Both enzymes are characterized in having high activity in an acidic range and no activity at around a neutral range. Therefore, these enzymes may be able to be used in oil mills industries where these enzymes may be used in an acidic range. However, properties in citric acid have never been described, and therefore it is unclear whether they can actually be used in oil mills industries (see Patent Document 3 and Nonpatent Document 7). In addition, the activity at pH 6 is near zero and it is difficult to use these enzymes in the food industries where enzyme reactions are often carried out at around neutral pH (see Patent Document 3).

Furthermore, it has been described that the phospholipase C enzymes produced by *Aspergillus niger* have an extremely high degradation activity of phosphatidic acid, a substrate of phosphatase (see Patent Document 3). Therefore, these enzymes are presumed to be proteins that also have a phosphatase activity, since they have an ability to hydrolyze a phosphoric acid monoester. Furthermore, it has been described that the phospholipase C enzymes produced by *Aspergillus saitoi* have an extremely high degradation activity of 2-hexadecanoylamino-4-nitrophenyl phosphorylcholine (see Nonpatent Document 7). Therefore, these enzymes are presumed to be proteins additionally to have an ability to hydrolyze any phosphodiesters except for phospholipid. Therefore, it is possible for the properties of foods processed using these enzymes to be changed unexpectedly.

Thus, the phospholipase C enzymes known conventionally do not have sufficient properties as enzymes, or have safety problems, and so forth, and thus no enzyme preparations containing phospholipase C enzymes have been in the market until now. Enzyme preparations having the desirable properties include ones being derived from microorganisms that already have the actual production results as enzyme preparations for foods, having an ability to hydrolyze various phospholipids efficiently both in an acidic range and at around neutral range, having the activity also in a citrate buffer solution to be usable also in oil mills industries, and having some degree of heat stability. Furthermore, the phospholipase C enzymes having a property not to hydrolyze any phosphate esters except for a phospholipid, typified by glycerophosphorylcholine, are included.

DISCLOSURE OF THE INVENTION

Problems to be Solved by the Invention

As described above, the desirable properties of phospholipase C enzymes include ones having an ability to hydrolyze various phospholipids efficiently both at acidic and at around neutral ranges, having an activity also in a citrate buffer solution to be usable also in oil mills industries, and having some degree of heat stability. Furthermore, phospholipase C enzymes, having a property not to hydrolyze any phosphate esters except for a phospholipid, typified by glycerophosphorylcholine, more preferably, phospholipase C enzymes derived from microorganisms that already have the actual production results in enzyme preparations for foods, are included.

Providing such phospholipase C enzymes have been greatly concerned in this technical field.

Means for Solving the Problem

As a result of keen studies to find phospholipase C enzymes having excellent safety, an ability to hydrolyze various phospholipids efficiently both at acidic ranges and at around neutral ranges, an activity also in a citrate buffer solution, some degree of heat stability, and a property not to hydrolyze any phosphate esters except for a phospholipid, the present inventors have purified phospholipase C enzymes derived from *Aspergillus oryzae* strain FERM BP-10200 or strain NBRC 4190, or *Aspergillus tamari* strain IAM 13907 and cloned a phospholipase C enzyme(s) gene derived from *Aspergillus oryzae* strain NBRC 4190, and thus completed the present invention.

That is, the present invention relates to (1) a phospholipase C enzyme(s) having the activity at from acidic to neutral pH and substantially not hydrolyzing any phosphate esters except for phospholipids, (2) the phospholipase C enzyme(s) in (1), being nonspecific to phosphatidylinositol, (3) the phospholipase C enzyme(s) in (1) or (2), its optimum pH being from pH 3 to pH 6, (4) the phospholipase C enzyme(s) in any one of (1)-(3), its relative activity at pH 7 being 20% or more, (5) the phospholipase C enzyme(s) in any one of (1)-(4), being produced by filamentous fungi, (6) the phospholipase C enzyme(s) in (5), filamentous fungi being *Aspergillus*, (7) the phospholipase C enzyme(s) in (6), being produced by *Aspergillus oryzae* or *Aspergillus tamari*, (8) the phospholipase C enzyme(s) in (7), being produced by *Aspergillus oryzae* strain FERM BP-10200 or strain NBRC 4190, or *Aspergillus tamari* strain IAM 13907, (9) the phospholipase C enzyme(s) of any one in (1)-(8), having the following properties:

1) molecular weight of approximately 87,000, determined by SDS-PAGE electrophoretic analysis;
2) hydrolyzing phosphatidylcholine, phosphatidylethanolamine, phosphatidylinositol and phosphatidylglycerol;
3) substantially not hydrolyzing glycerophosphorylcholine and p-nitrophenylphosphate;
4) hydrolyzing egg yolk lecithin within the range of from pH 3 to pH 9;
5) having hydrolyzing activity in 4) within the range of from 0° C. to 80° C.;
6) having temperature/stability at temperatures of 45° C. or below at pH 4.5; and
7) having pH/stability within the range of from pH 3 to pH 10,

(10) a phospholipase C enzyme(s), being a protein of any one of the following a)-d):

a) a protein consisting of the amino acid sequence of SEQ ID NO: 5;
b) a protein consisting of the amino acid sequence encoded by the nucleotide sequence of SEQ ID NO: 4;
c) a protein consisting of the amino acid sequence in a) or b), having one or several amino acids deleted, replaced or added, and characterized in having the phospholipase C activity; and
d) a protein comprising the amino acid sequence in a) or b),

(11) Filamentous fungi belonging to isolated *Aspergillus oryzae* or *Aspergillus tamarii*, having an ability to produce the phospholipase C enzyme(s) in any one of (1)-(4), (9) and (10), providing that *Aspergillus tamari* strain IAM 13907 is excluded,

(12) Filamentous fungus in (11), its strain being *Aspergillus oryzae* strain FERM BP-10200 or strain NBRC 4190,

(13) DNA in any one of the followings a)-d):

a) DNA consisting of the nucleotide sequence of the coding region (CDS) of SEQ ID NO: 4;
b) DNA consisting of the nucleotide sequence having 70% or more of nucleotide sequence homology with the DNA in the above a), and characterized in coding a protein having the phospholipase C activity;
c) DNA encoding a protein consisting of the amino acid sequence of SEQ ID NO: 5; and
d) DNA comprising the nucleotide sequence of the coding region (CDS) of SEQ ID NO: 4,

(14) the phospholipase C enzyme(s), its protein being encoded by the DNA in (11),

(15) A method for producing phospholipase C, comprising 1) a step for culturing the *Aspergillus oryzae* or *Aspergillus tamarii* in (9) and
2) a step for isolating/purifying a phospholipase C enzyme(s) from the culture in 1),

(16) A method in (15), *Aspergillus oryzae* being *Aspergillus oryzae* strain FERM BP-10200, or strain NBRC 4190, and *Aspergillus tamarii* being *Aspergillus tamarii* strain IAM 13907,

BEST MODE FOR CARRYING OUT THE INVENTION

Figure 1:
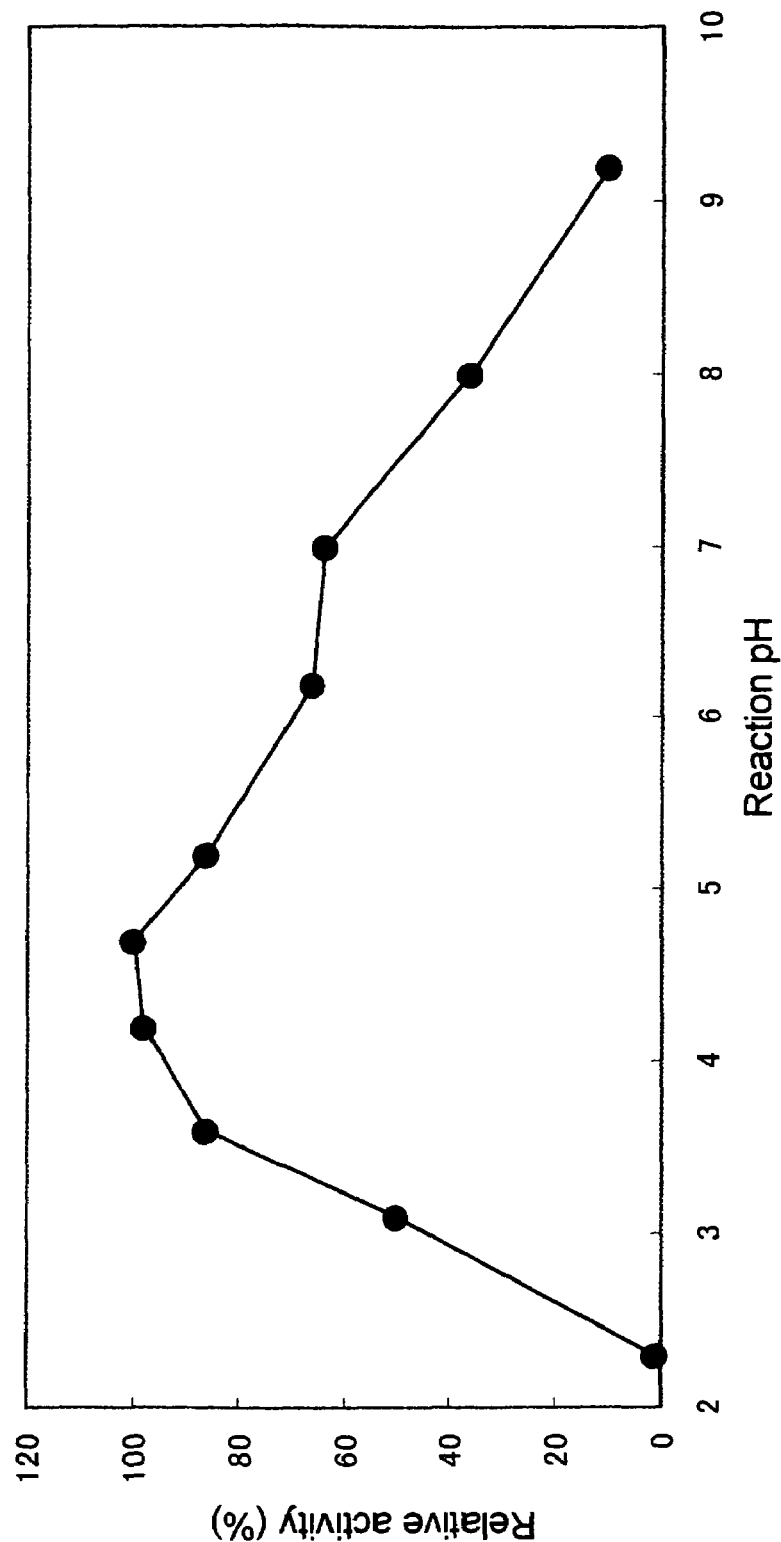
FIG. 1 is a figure showing a relationship between the activity of the purified the phospholipase C enzyme(s) derived from *Aspergillus oryzae* strain FERM BP-10200 and pH.

Hereinafter, the present invention will be described in detail. As long as indicated otherwise, the methods for measuring each property are in accordance with those described in the below-mentioned Examples or Test Examples.

The present invention relates to a phospholipase C enzyme(s) having the activity at from acidic to neutral pH and substantially not hydrolyzing any phosphate esters except for phospholipid, or to a phospholipase C enzyme(s) having the activity at from acidic to neutral pH and no phosphatase activity.

The term "activity at from acidic to neutral pH" refers to 20% or more of relative activity at the range of from pH 3 to pH 7, the method for measuring enzyme activity being in accordance with "Test Example 1-1) pH/activity".

The term "substantially not hydrolyzing any phosphate esters except for phospholipids" refers to the hydrolyzing activity, shown as a relative value to 100% of the hydrolyzing activity of phosphatidylcholine (extracted from egg yolk), being preferably 30% or less, and more preferably 25% or less in a case of hydrolyzing phosphatidic acid; and/or preferably 15% or less, and more preferably 10% or less in a case of hydrolyzing glycerophosphorylcholine; and/or 10% or less, and more preferably 5% or less in a case of hydrolyzing p-nitrophenylphosphate. The same can be said for "substantially not hydrolyzing glycerophosphorylcholine and p-nitrophenylphosphate".

Phosphatidic acid should not be included in glycerophospholipid (phospholipid) herein, since it is regarded as a synthetic intermediate of neutral fat or glycerophospholipid.

The term "having no phosphatase activity" refers to 50% or less of the degradation activity for phosphatidic acid or p-nitrophenylphosphate, relative to the degradation activity for phosphatidylcholine; and the degradation activity for phosphatidic acid, relative to the degradation activity for phosphatidylcholine, is preferably 40% or less, more preferably 30% or less, and most preferably 25% or less. The degradation activity for p-nitrophenylphosphate, relative to the degradation activity for phosphatidylcholine, is preferably 30% or less, more preferably 20% or less, and most preferably 10% or less.

The phospholipase C enzyme(s) of the present invention has the degradation activity for sphingomyelin; and the degradation activity is preferably comparable similar to or higher than the degradation activity for phosphatidylcholine. Specifically, the degradation activity for phosphatidylcholine, shown as a relative value to 100% of the degradation activity for phosphatidylcholine (extracted from egg yolk), is preferably 90% or more, more preferably 105% or more, and most preferably 115% or more.

The phospholipase C enzyme(s) of the present invention has the degradation activity for phosphatidylethanolamine; and the degradation activity is preferably similar to that for phosphatidylcholine. Specifically, the degradation activity for phosphatidylethanolamine, shown as a relative value to 100% of the degradation activity for phosphatidylcholine (extracted from egg yolk), is preferably 80% or more, more preferably 85% or more, and most preferably 90% or more and 150% or less.

The term, a phospholipase C enzyme(s) being "phosphatidylinositol-nonspecific" means a high degradation activity (relative activity) for any substrates except for phosphatidylinositol, as compared with that for phosphatidylinositol. The substrates except for phosphatidylinositol herein include preferably phosphatidylcholine, phosphatidylethanolamine, phosphatidylinositol, and phosphatidylglycerol.

The optimum pH of the phospholipase C enzyme(s) of the present invention is preferably within the range of from acidic to neutral pH, more preferably within the range of from pH 3 to pH 6, more preferably within the range of from pH 3 to pH 5, and most preferably within the range of from pH 4 to pH 5.

The term "relative activity at pH 7" refers to the percentage (%) of the hydrolyzing activity of the enzyme at pH 7 shown as a relative value to 100% of the maximum hydrolyzing activity at the certain pH. The relative activity of the phospholipase C enzyme(s) of the present invention at pH 7 is preferably 20% or more, more preferably 40% or more, and most preferably 50% or more.

As for the activity at various temperatures (activity/temperature), the phospholipase C enzyme(s) of the present invention has the optimum temperature preferably within the range of 45-70° C., more preferably within the range of 55-70° C., and most preferably within the range of 60-70° C. The relative activity of the phospholipase C enzyme(s) of the present invention is preferably 50% or more at 55-70° C., more preferably 50% or more at 45-70° C., and most preferably 50% or more at 35-70° C. The relative activity is preferably 80% or more at 55-65° C.

As for temperature/stability, the term "being stable" means having 40% or more of the residual hydrolyzing activity; and the residual hydrolyzing activity of the phospholipase C enzyme(s) of the present invention at treating temperature of 45° C. or below is preferably 50% or more, more preferably 70% or more, and most preferably 80% or more. The residual hydrolyzing activity of the phospholipase C enzyme(s) of the present invention is 40% or more preferably at treating temperature of 45° C., more preferably at treating temperature of 50° C., and most preferably at treating temperature of 60° C.

As for pH/stability, the term "being stable" means having 5% or more of the residual hydrolyzing activity after treating of storage; and the residual hydrolyzing activity of the phospholipase C enzyme(s) of the present invention at treating pH of from pH 5 to pH 9 is preferably 40% or more, more preferably 50% or more, and most preferably 60% or more. The residual hydrolyzing activity at treating pH of from pH 6 to pH 8 is preferably 60% or more, more preferably 70% or more, and most preferably 80% or more.

Another example of the phospholipase C enzyme(s) of the present invention includes proteins containing any one of sequences of SEQ ID NOS: 1, 2, and 3, preferably any two of them and most preferably all three of them, and having the phospholipase C activity. When the protein contains two or more of these three amino acid sequences, the amino acid sequences can be placed in any order.

In addition, proteins consisting of the amino acid sequence of SEQ ID NO: 5, having one or several amino acids deleted, replaced or added, and characterized in having the phospholipase C activity are also included in the present invention. As an example of a protein having a replaced amino acid sequence(S) and the activity similar to that of naturally occurring protein, for example proteins obtained by replacing the nucleotide sequence corresponding to a cysteine in an interleukin 2 (IL-2) gene with the nucleotide sequence corresponding to a serine is known to retain IL-2 activity (Wang, A. et al., (1984), Science 224, 1431-1433).

A protein consisting of the amino acid sequence of SEQ ID NO: 5 may be included as another example of the phospholipase C enzyme(s) of the present invention. A protein comprising the amino acid sequence of SEQ ID NO: 5 is also included in the present invention as long as it has the phospholipase C activity.

As another example of the phospholipase C enzyme(s) of the present invention, a glycosylated protein consisting of the amino acid sequence of SEQ ID NO: 5 is included. A protein comprising such protein is also included in the present invention as long as it has the phospholipase C activity.

The phospholipase C enzyme(s) of the present invention is preferably the phospholipase C enzyme(s) derived from *Aspergillus oryzae* strain FERM BP-10200 or strain NBRC 4190, or *Aspergillus tamarii* strain IAM 13907; a protein consisting of the amino acid sequence of SEQ ID NO: 5; or a glycosylated protein consisting of the amino acid sequence of SEQ ID NO: 5, more preferably, the phospholipase C enzyme(s) derived from *Aspergillus oryzae* strain FERM BP-10200 or strain NBRC 4190, or *Aspergillus tamarii* strain IAM 13907; or a glycosylated protein consisting of the amino acid sequence of SEQ ID NO: 5.

In the present invention, "DNA of the present invention" refers to DNA encoding the phospholipase C enzyme(s) of the present invention. The DNA may take any forms known up to now such as cDNA, genome DNA, artificially-modified DNA, chemically-synthesized DNA, etc.

An example of DNA of the present invention includes DNA having the nucleotide sequence of the coding region (CDS) of SEQ ID NO: 4 and encoding a protein having the phospholipase C activity.

Another example of DNA of the present invention includes DNA having 70% or more of nucleotide sequence homology with the nucleotide sequence of the coding region (CDS) of SEQ ID NO: 4. Such DNAs include naturally-occurring variant DNA, artificially-modified variant DNA, homologous DNA derived from different species, etc.

In addition, a further example of the nucleotide of the present invention includes DNA encoding the protein consisting of the amino acid sequence of SEQ ID NO: 4. The codon corresponding to the desired amino acid is optionally selected; and for example, it can be determined, according to standard methods, under consideration of the frequency of codon usage in a host used (Grantham, R. et al., (1981), Nucleic Acids Res., 9, 143-174). Furthermore, the codons of these nucleotide sequences can partially be modified by site specific mutagenesis (Mark, D. F. et al., (1984), Proc. Natl. Acad. Sci., USA 81, 5662-5666) and the like, according to standard methods, using primers consisting of synthetic oligonucleotides encoding the desired modification.

Another example of the DNA of the present invention includes DNA consisting of the nucleotide sequence of the coding region (CDS) of SEQ ID NO: 4. In addition, DNA containing the nucleotide sequence of the coding region (CDS) of SEQ ID NO: 4 is also included as long as it encodes a protein having the phospholipase C activity.

In addition, the phospholipase C enzyme(s) of the present invention includes a protein comprising the amino acid sequence encoded by the DNA of the present invention. To produce a variant having one, two or more arbitrary amino acids deleted in the phospholipase C enzyme(s) of the present invention, a method for deleting DNA from the termini using exonuclease Bal31, etc. (Toshimitsu Kishimoto et al., "Zoku-Seikagaku Jikken Kouza 1: Idenshi Kenkyuho II", 335-354), a cassette mutation method (Toshimitsu Kishimoto, "Shin-Seikagaku Jikken Kouza 2: Kakusan III Kumikae DNA Gijutsu," 242-251) and the like, can be used. Thus, a protein obtained by a genetic engineering technique based on the DNA of the present invention is also included in the present invention as long as it has the phospholipase C activity. Such phospholipase C enzyme(s) does not necessarily need to have the entire amino acid sequence of SEQ ID NO: 5; for example, a protein comprising the partial sequence is also included in the phospholipase C enzyme(s) of the present invention as long as it exhibits the phospholipase C activity. DNA encoding such phospholipase C enzyme(s) is also included in the present invention.

The phospholipase C enzyme(s) used for the present invention may be purified phospholipase C enzyme(s) from phospholipase C-producing fungi, partially purified phospholipase C enzyme(s) from phospholipase C-producing fungi or a crushed-fungi solution as well as a supernatant of fungi culture in itself. When phospholipase C-producing fungi are cultured, the culture can be preferably carried out by adding carbon and nitrogen sources as well as a surfactant into the culture medium. Or the culture can be preferably carried out in an unartificial culture medium such as fish powders, ground sesames, or cottonseed lees. The surfactants include Triton, Tween, sucrose fatty acid ester, sodium cholate, sodium deoxycholate, saponin, etc.

The phospholipase C-producing fungi can be cultured using a usual culture apparatus and a culture medium. A culturing method such as liquid culture or solid culture may be selected as needed. Liquid culture can be carried out using a flask or a fermenter; and after the culture is started, batch culture without adding further culture medium, or fed batch culture with adding culture medium as needed during culturing, can be employed. Carbon and nitrogen sources are added to the medium, and vitamins, trace metal elements, etc., may be added as needed. The carbon sources include monosaccharides such as glucose, mannose, galactose and fructose; disaccharides such as maltose, cellobiose, isomaltose, lactose and sucrose; polysaccharides such as starch; and malt extract, etc. The nitrogen sources include inorganic nitrogens such as ammonia, ammonium sulfate and ammonium nitrate; and organic nitrogens such as yeast extract, malt extract, corn steep liquor and peptone may be used. The amounts of the composition in these media can be selected as needed. Incubation temperature, pH, and the volume of aeration and stirring may be selected as needed to produce properly the phospholipase C enzyme(s).

After the completion of culturing, the culture solution containing the phospholipase C-producing fungi is centrifuged, and the culture supernatant, from which the fungi removed, can directly be used as a crude enzyme solution. Or, a partially purified product or a purified product, obtained by purifying a crude enzyme solution using exchange chromatography, etc., may be used.

The *Aspergillus oryzae* strain FERM BP-10200 or strain NBRC 4190, or *Aspergillus tamarii* strain IAM 13907 of the present invention include all mutants thereof, as long as they can produce the phospholipase C enzyme(s) of the present invention. These mutants include those obtained by genetic methods such as recombination, transduction, transformation, etc. Namely, all of *Aspergillus oryzae* strain FERM BP-10200 or strain NBRC 4190, or *Aspergillus tamarii* strain IAM 13907, mutants thereof and the strains that cannot clearly be distinguished from the *Aspergillus* strains, producing the phospholipase C enzyme(s) of the present invention, are included in *Aspergillus oryzae* strain FERM BP-10200 or strain NBRC 4190, or *Aspergillus tamarii* strain IAM 13907.

The phospholipase C enzyme(s) of the present invention can be obtained from the culture of the transformed cells obtained by transforming host cells with a recombinant plasmid of which vector is inserted with the DNA of the present invention. Therefore, the recombinant plasmid of which suitable vector is inserted with the DNA of the present invention, is also included in the present invention. Heretofore known various vectors can be used as vectors used for this purpose. Preferable vectors include, but are not limited to, vectors for prokaryotic cells, vectors for eukaryotic cells, and vectors for animal cells. Various prokaryotic and eukaryotic host cells can be transformed with such recombinant plasmids. Furthermore, it is possible to express a gene in each host by using a vector carrying a suitable promoter sequence and/or a sequence related to phenotypic expression, or by introducing such sequence to prepare an expression vector. Such an expression vector is a preferable embodiment of the recombinant plasmid of the present invention.

Host cells can be obtained by introducing the recombinant plasmid of the present invention into various cells. Such cells may be prokaryotic or eukaryotic cells, as long as they are cells into which the plasmid can be introduced.

Prokaryotic host cells include, for example, *Escherichia coli, Bacillus subtilis*, etc. For the transformation of these host cells with a target gene, the host cells are transformed with a plasmid vector containing a host-compatible replicon (i.e., replication origin) and a regulatory sequence derived from the species. Besides, a sequence that can confer selectivity of phenotypic property (phenotype) to the transformed cells is preferred as a vector.

For nonlimiting example, strain K12, etc., is commonly used as *Escherichia coli*, and pBR322 and pUC plasmids are generally used as vectors; and, heretofore known various strains and vectors can also be used.

The promoters include tryptophan (trp) promoter, lactose (lac) promoter, tryptophan/lactose (tac) promoter, lipoprotein (lpp) promoter, polypeptide chain extension factor Tu (tufB) promoter, etc.; and all the promoters can be used for the production of the phospholipase C enzyme(s) of the present invention.

For nonlimiting example, strain 207-25 is preferable as *Bacillus subtilis*, and pTUB228 (Ohmura, K. et al., (1984), J. Biochem., 95, 87-93), etc., are used as vectors.

The secretory expression outside of cells can also be achieved by linking a DNA sequence encoding the signal peptide sequence of α-amylase of *Bacillus subtilis* to a promoter.

The eukaryotic host cells include cells of vertebrates, insects, yeasts, etc.; and mammalian cells such as COS cells derived from a monkey (Gluzman, Y. (1981) Cell 23, 175-182, ATCC CRL-1650) or Chinese hamster ovary cells (CHO cells, ATCC CCL-61), etc., of dihydrofolate reductase-deficient strain (Urlaub, G. and Chasin, L. A., (1980), Proc. Natl. Acad. Sci., USA 77, 4126-4220), can be used as vertebrate cells.

In general, an expression promoter having a promoter located upstream of the gene to be expressed, RNA splice junction, polyadenylation region, transcription-termination sequence, etc., can be used as an expression promoter in vertebrate cells, and this may have a replication origin as needed. The expression vectors include, but not limited to, pSV2dhfr having SV40 early promoter (Subramani, S. et al., (1981), Mol. Cell. Biol., 1, 854-864), etc.

For example, in using COS cells as host cells, an expression vector having SV40 replication origin, being autonomously replicable in COS cells, and providing with transcription promoter, transcription termination signal and RNA splice junction, can be used. The expression vector can be introduced into COS cells by diethylaminoethyl (DEAE)-dextran method (Luthman, H. and Magnusson, G., (1983), Nucleic Acids Res, 11, 1295-1308), calcium phosphate-DNA coprecipitation method (Graham, F. L. and van der Eb, A. J., (1973), Virology, 52, 456-457), electroporation method (Neumann, E. et al., (1982), EMBO J., 1, 841-845), etc., to obtain the desired transformed cells. In addition, when CHO cells are used as host cells, transformed cells, producing stably the phospholipase C enzyme(s) of the present invention can be obtained by cotransfecting a vector that may express a neo gene that functions as an antibiotics G418 resistance marker (e.g., pRSVneo (Sambrook, J. et al., (1989): "Molecular Cloning A Laboratory Manual", Cold Spring Harbor Laboratory, NY) or pSV2-neo (Southern, P. J. and Berg, P., (1982), J. Mol. Appl. Genet., 1, 327-341)) together with the expression vector, and by selecting G418 resistant colonies.

When insect cells are used as host cells, ovarian cell-derived established cell line of *Spodoptera frugiperda* (Lepidoptera: Noctuidae) (Sf-9 or Sf-21), egg cell-derived High Five cells of *Trichoplusia ni* (Wickham, T. J. et al., (1992), Biotechnol. Prog., I: 391-396), etc., are commonly used as host cells; and pVL1392/1393 using the promoter of the Pori Hedrin protein of *Autographa californica* nucleopolyhedrovirus (AcNPV) are commonly used as a Baculoviridae transfer vector (Kidd, I. M. and V. C. Emery, (1993): "The use of baculoviruses as expression vectors", Applied Biochemistry and Biotechnology, 42, 137-159). In addition, a vector using a baculovirus P10 promoter or its basic protein promoter can also be used. Furthermore, a recombinant protein can also be expressed as a secretory protein by linking the secretion signal sequence of envelope surface protein GP67 of AcNPV to the N-terminal residue of a protein of interest (Zhe-mei Wang, et al., (1998), Biol. Chem., 379, 167-174).

Yeasts are generally known well as an expression system using a eukaryotic microorganism as host cells; and particularly, *Saccharomyces* yeasts such as baker's yeast *Saccharomyces cerevisiae* and petroleum yeast *Pichia pastoris* are preferable. For expression vectors of eukaryotic microorganisms such as these yeasts, for examples, the promoter of an alcohol dehydrogenase gene (Bennetzen, J. L. and Hall, B. D., (1982), J. Biol. Chem., 257, 3018-3025), the promoter of an acid phosphatase gene (Miyanohara, A. et al., (1983), Proc. Natl. Acad. Sci., USA 80, 1-5), etc., can preferably be used. In addition, for the expression of a secretory protein, it is also possible to express a recombinant having a secretion signal sequence and a cleavage site of an endogenous protease or a known protease of host cells at the N-terminal residue. For example, it is known that active tryptase will be secreted into a medium by linking the secretion signal sequence of a factor of yeast and the cleavage site of KEX2 protease of petroleum yeast at the N-terminal residue in a system to express human mast cell tryptase of trypsin type serine protease in petroleum yeast (Andrew, L. Niles, et al., (1998), Biotechnol. Appl. Biochem., 28, 125-131).

The transformant obtained above can be cultured by conventional methods, and the phospholipase C enzyme(s) of the present invention is produced inside or outside of the cells by this culture. Various culture media commonly used for the culture according to host cells used, can be selected as needed; and for example, media such as RPMI1640 medium and the Dulbecco's Modified Eagle's Medium (hereinafter "DMEM"), to which serum components such as fetal bovine serum are added as needed, can be used for the above COS cells. As for culture conditions, $CO_2$ concentration may be 0-50%, preferably 1-10%, and more preferably 5%. The culture temperature may be 0-99° C., preferably 20-50° C. and more preferably 35-40° C.

The phospholipase C enzyme(s) of the present invention, produced as a recombinant protein inside or outside of the cells in the above culture, can be isolated and purified from the culture product by various isolation procedures using said protein's physicochemical, chemical, and biochemical properties (enzyme activity, etc.) and the like (see "Biochemistry Data Book II", 1st edition 1st print, p 1175-1259, Jun. 23, 1980, Tokyo Kagaku Dojin Issue; Biochemistry, vol. 25, No. 25, p 8274-8277 (1986); Eur. J. Biochem., 163, p 313-321 (1987), etc.). Specifically, examples of these methods include usual reconstruction treatment, protein precipitant treatment (salting-out method), centrifugation, osmotic shock method, freezing and thawing method, sonication, ultrafiltration, gel filtration, various liquid chromatography such as absorption chromatography, ion exchange chromatography, affinity chromatography and high performance liquid chromatography (HPLC), dialysis, combinations thereof, etc. Using the above, the desired recombinant protein can be produced in high yields and in an industrial scale. Additionally, the recombinant protein linked to 6 histidine residues can be purified effectively by a nickel affinity column. By combinations of the above methods, the phospholipase C enzyme(s) of the present invention can be easily produced in high yield, at high purity and in a large quantity.

The phospholipase C enzyme(s) produced by the above methods can also be mentioned as a preferred example of the present invention.

A phospholipase C-producing fungi refers to microorganisms substantially having the phospholipase C producing ability, including microorganisms that accumulate the phospholipase C enzyme(s) within the cells or secret the phospholipase C enzyme(s) outside of the cells. When a culture supernatant of the phospholipase C-producing fungi or the phospholipase C enzyme(s) purified from a culture supernatant is used, fungi secreting the phospholipase C enzyme(s) outside of the cells can be used.

As the phospholipase C enzyme(s) used for the present invention, the phospholipase C enzyme(s) derived from *Aspergillus oryzae* or *Aspergillus tamarii*, and more preferably, the phospholipase C enzyme(s) derived from *Aspergillus oryzae* strain FERM BP-10200 or strain NBRC 4190, or *Aspergillus tamarii* strain IAM 13907 can be used. The phospholipase C enzyme(s) may be a protein produced by phospholipase C-producing fungi themselves, or variants or modified one thereof, or a recombinant protein produced from a transformant obtained by introducing a gene encoding the phospholipase C enzyme(s) of these phospholipase C-producing fungi into a host.

Procurement of Phospholipase C-Producing Fungi

*Aspergillus oryzaes* strain NBRC 4190 can be procured from the NITE (National Institute of Technology and Evaluation) Biological Resource Center (2-5-8 Kazusa-kamatari, Kisarazu, Chiba 292-0818, Japan, HP <http://www.nite.go.jp/>).

*Aspergillus tamarii* strain IAM 13907 (=IAM 13907) can be procured from the Institute of Molecular and Cellular Biosciences, The University of Tokyo (1-1-1, Yayoi, Bunkyo-ku 113-0032, Tokyo, HP <http://www.iam.u-tokyo.ac.jp/indexe.html>).

Morphological properties of *Aspergillus oryzae* strain FERM BP-10200 are shown below.

*Aspergillus oryzae* strain FERM BP-10200 was inoculated into four media (CYA medium, CY20S medium, CZ medium, and MEA medium), according to the literature of Klich (Klich, M. A., (2002), Identification of common *Aspergillus* Centraalbureau voor Schimmelcultures, Utrecht, The Netherlands) to observe the morphological properties.

Color tones are indicated according to "Methuen handbook of color" (Kornerup, A. and Wanscher, J. H., (1978): Methuen handbook of color (3rd edition), Erye Methuen, London.).

The compositions of the four culture media (CYA medium, CY20S medium, CZ medium, and MEA medium) are as follows:

CYA Medium [Czapek Yeast Extract Agar Medium]
($K_2HPO_4$ 1.0 g, * Czapek concentrated solution 10 ml, yeast extract 5 g, sucrose 30 g, agar 15 g, distilled water 1,000 ml)

* Czapek concentrated solution ($NaNO_3$ 30 g, KCl 5 g, $MgSO_4.7H_2O$ 5 g, $FeSO_4.7H_2O$ 0.1 g, $ZnSO_4.7H_2O$ 0.1 g, $CuSO_4.5H_2O$ 0.05 g, distilled water 100 ml)

CY20S medium [Czapek Yeast Extract Agar with 20% Sucrose medium]
($K_2HPO_4$ 1.0 g, * Czapek concentrated solution 10 ml, yeast extract 5 g, sucrose 200 g, agar 15 g, distilled water 1,000 ml)

CZ Medium [Czapek Dox Agar Medium]
($K_2HPO_4$ 1.0 g, * Czapek concentrated solution 10 ml, sucrose 30 g, agar 17.5 g, distilled water 1,000 ml)

MEA Medium [Malt Extract Agar Medium]
(malt extract 20 g, peptone 1 g, glucose 20 g, agar 20 g, distilled water 1,000 ml)

1) Morphological Properties

Morphological Properties of *Aspergillus oryzae* Strain FERM BP-10200

The diameter of the colonies in CYA medium was 36-40 mm after 1 week culture at 25° C. The colonies were slightly thick and wool-like, and cotton wool-like in the central part, forming a radial groove from the central part. The hyphae was white. Conidia were formed sparsely in the central part, showing ashy yellow (4B4) to yellow white (4A2). Neither exudation nor sclerotium was observed. The back side (of the strain) was light yellow (2A4) to white (2A1), forming a radial groove from the central part. No soluble pigment was observed.

The diameter of the colonies in CYA medium was 54-58 mm after 1 week culture at 37° C. The colonies were thick and wool-like. The hyphae was white. Conidia were formed in the central part, showing ashy yellow (4B4) to yellow white (4A2). Neither exudation nor sclerotium was observed. The back side (of the strain) was light orange (4A4) to white (4A2), forming a radial groove from the central part. No soluble pigment was observed.

The diameter of the colonies in CY20S medium was 35-41 mm after 1 week culture at 25° C. The aspect of the colonies was similar to that in CYA medium, but there were slightly more cotton wool-like hyphae in the central part.

The diameter of the colonies in CZ medium was 17-21 mm after 1 week culture at 25° C. The aspect of the colonies was similar to that in CYA medium, but the colonies were smaller, and conidia were formed sparsely.

The diameter of the colonies in MEA medium was 37-41 mm after 1 week culture at 25° C. The colonies were thin and cotton wool-like. The hyphae was white. Conidia were formed sparsely in the central part, showing dark green (26D4) to ashy green (26D6). Neither exudation nor sclerotium was observed. The back side (of the strain) was ashy yellow (4B3) to yellow white (4A2), and no soluble pigment was observed.

The colonies were grown at 14-42° C.; conidia were observed to be formed at 18-38° C.

The conidial head took a radial to loosely cylindrical form. The conidiophores were 6.7-13.6 μm in width, 302.2-1398.0 μm in length, colorless, and had rough surfaces. The vesicles took a subspheric to flask form and was 14.6 to 29.3 μm in width. *Aspergilla* were mainly uniseriate, and rarely biseriate. Metula or phialides were formed from the top halves of vesicles. The metula were 11.3-28.3×5.2-9.9 μm. The phialides were 8.4-21.3×3.8-7.7 μm in a flask form. The conidia had smooth surfaces, taking an oval to subspheric form, and were 4.2-6.3 μm in diameter.

A search for an organism that falls into the fungi of interest demonstrated that the above morphological properties almost conformed to those of *Aspergillus oryzae* (Ahlburg) Chon, described in Klick's literature. Thus, strain FERM BP-10200 was identified as *Aspergillus oryzae* (Ahlburg) Chon and deposited in the International Patent Organism Depositary, National Institute of Advanced Industrial Science and Technology, AIST Tsukuba Central 6, 1-1 Higashi 1-chomme, Tsukuba-shi, Ibaraki-ken 305-8566 Japan, deposited on Jan. 6, 2005.

The specific properties of the phospholipase C enzyme(s), obtained from the phospholipase C-producing fungi, are shown below; but the properties of the phospholipase C enzyme(s) of the present invention are not necessarily limited to these.

The phospholipase C enzyme(s), produced by *Aspergillus oryzae* strain FERM BP-10200 or strain NBRC 4190, or *Aspergillus tamarii* strain IAM 13907 and purified, has the following properties:

1) Having approximately 87,000 of molecular weight determined by SDS-PAGE electrophoretic analysis
2) Hydrolyzing egg yolk lecithin (Nacalai Tesque, Inc.) at from pH 3 to pH 9,
3) Having the hydrolyzing activity described in 4) at 0-80° C.,
4) Being stable at 45° C. or below at pH 4.5,
5) Being stable at from pH 3 to pH 10,
6) Optimum pH for the hydrolyzing activity described in 2) being pH 4.5,
7) Optimum temperature for the hydrolyzing activity described in 3) at pH 4.5 being 65° C.,
8) Hydrolyzing phosphatidylcholine, phosphatidylethanolamine, phosphatidylinositol and phosphatidylglycerol, but substantially not hydrolyzing glycerophosphorylcholine and p-nitrophenylphosphate.

As one example, (hydrolyzing) activities, shown as relative values to 100% of (activity of hydrolyzing) phosphatidylcholine derived from egg yolk, are shown in Table 1. For substrates derived from egg yolk or soybean, the derivations are described in Table. The egg yolk lecithin was purchased from Nacalai Tesque, Inc., and the soybean lecithin was purchased from Tsuji Oil Mill Co. Ltd., and the other substrates were purchased from SIGMA-ALDRICH Japan K.K.

TABLE 1

| Substrates | Relative activity (%) |
|---|---|
| Phosphatidylcholine (egg yolk) | 100 |
| Phosphatidylethanolamine (egg yolk) | 101 |
| Phosphatidylglycerol (egg yolk) | 162 |
| Phosphatidic acid (egg yolk) | 17 |
| Lecithin (egg yolk) | 88 |
| Lysophosphatidylcholine (egg yolk) | 41 |
| Glycerophosphorylcholine (soybean) | 5 |
| p-Nitrophenylphosphate | 0 |
| Phosphatidylcholine (soybean) | 94 |
| Phosphatidylethanolamine (soybean) | 90 |
| Phosphatidylinositol (soybean) | 59 |
| Lecithin (soybean) | 82 |

TABLE 1-continued

| Substrates | Relative activity (%) |
|---|---|
| Sphingomyelin (bovine brain) | 121 |
| Sphingomyelin (egg yolk) | 125 |

9) Having the partial amino acid sequence shown below where a sequence is indicated from the N-terminal residue:

(SEQ ID NO: 1)
Thr-Ala-Asp-Ser-Ala-Thr-Ala-Ile-Gly-Tyr-Val-Thr-Pro-Ser-Met, (SEQ ID NO: 2)
Glu-Ala-Tyr-Gly-Ser-Leu-Leu-Thr-Pro-Pro, (SEQ ID NO: 3)
Val-Pro-Pro-Ser-His-Asn-Pro-Gln-Trp-Ala,

10) Protein being glycosyled.

Based on the above, the properties of the phospholipase C enzyme(s) of the present invention include, but not limited to, the followings:

1) Having Approximately 87,000 of molecular weight determined by SDS-PAGE electrophoretic analysis;
2) Hydrolyzing egg yolk lecithin (Nacalai Tesque, Inc.) at from pH 3 to pH 9;
3) Having the hydrolyzing activity described in 4) at from 0° C. to 80° C.;
4) Being stable at 45° C. or below at pH 4.5; and
5) Being stable at from pH 3 to pH 10.

In addition, the method for manufacturing the phospholipase C enzyme(s) of the present invention is also included in the present invention.

By culturing phospholipase C-producing microorganisms, including *Aspergillus oryzae* strain FERM BP-10200 or strain NBRC 4190, or *Aspergillus tamarii* stain IAM 13907 in a culture medium, the phospholipase C enzyme(s) can be produced. For example, shaking culture is carried out at 100-250 rpm for 1-15 days at from 16° C. to 45° C. in a medium with 0.1-5.0% polypeptone (Wako Pure Chemical Industries, Ltd.) and 0.1-1.0% yeast extract (Nippon Becton Dickinson Company, Ltd.), adding 0.05-1.0% sodium deoxycholate thereto, a medium with 0.1-4.0% Pharmamedia (TRADERS PROTEIN Inc.), adding 0.05-1.0% Triton X-100 (SIGMA-ALDRICH Japan K.K.) or 0.05-0.3% egg yolk lecithin thereto, or a medium with 10% fish meal (Kiichiro Ikeguchi Store).

EXAMPLES

Examples and test examples are indicated below, but the scope of the present invention is not limited to these.

Example 1

Purification of Phospholipase C Enzyme(s) from *Aspergillus oryzae* Strain FERM BP-10200

1) Preparation of a Crude Enzyme Solution

To a 500 ml vol. Erlenmeyer flask (seed flask) containing 100 ml of sterilized medium having the composition in Table 2, 1 ml of 5% filter-sterilized sodium deoxycholate solution was added and *Aspergillus oryzae* strain FERM BP-10200 was inoculated, and shaking culture was carried out at 170 rpm and at 26° C. for 7 days.

TABLE 2

| Medium | |
|---|---|
| Polypeptone | 40 g |
| Yeast extract | 5 g |
| Dipotassium hydrogen phosphate | 0.2 g |
| Magnesium sulfate | 0.5 g |

Purified water added to adjust the volume to 1,000 ml.

After culture, centrifugation was carried out at 10,000×G and at 4° C. for 10 minutes. The obtained supernatant was used as a crude enzyme solution.

2) Method for Measuring Enzyme Activity

The hydrolyzing activity of the phospholipase C enzyme (s) was measured as follows:

<1> Hydrolysis Reaction of Lecithin

To 60 µl of a substrate solution in which 1.5 g of egg yolk lecithin (Nacalai Tesque, Inc.) was dissolved in 50 ml of 4% (wt/v) TritonX-100, 60 µl of 200 mM acetic acid buffer solution (pH 5.5) were added and kept at 37° C. To this mixture, 60 µl of an enzyme solution was added and stirred to be homogeneous, and the enzyme reaction was carried out at 37° C. for 3 hours.

<2> Hydrolysis Reaction of Phosphoryl Base Resulting from The Enzyme Reaction

The phosphoryl base resulting from the enzyme reaction was hydrolyzed by alkaline phosphatase. To 50 µl of the enzyme reaction solution prepared in <1>, 50 µl of 200 mM Tris-HCl buffer solution. (pH 8.0) and 1 µl of alkaline phosphatase (SIGMA-ALDRICH Japan K.K.) were added, and the reaction was carried out at 37° C. for 40 minutes. In addition, a sample without addition of alkaline phosphatase was prepared as a blank at this time.

<3> Quantification of Inorganic Phosphorus Acid

The inorganic phosphorus resulting from <2> was measured by Phospha C Test Wako (Wako Pure Chemical Industries, Ltd.). To 100 µl of the reaction solution obtained in <2>, 1 ml each of A and B solutions of Phospha C Test Wako were added, and the reaction was carried out at 37° C. for 20 minutes. The absorbance at 750 nm of this mixture was measured. The difference of the absorbance between the mixture and the blank shows the phospholipase C activity. Enzyme activity that generates 1 µmol of phosphoryl base per minute by the enzyme reaction was regarded as one unit.

3) Preparation of a Purified Enzyme Solution 1,200 ml of the crude enzyme solution obtained in 1) were dialyzed 8 times for every 12 hours in 8,000 ml of 10 mM Tris-HCl buffer solution (pH 7.5). This was added and adsorbed to a DEAE TOYOPEARL (TOSOH CORP.) column (2.2 cm in diameter×20 cm in length) equilibrated in advance with 10 mM Tris-HCl buffer solution (pH 7.5). After the column was washed sufficiently with 10 mM Tris-HCl buffer solution (pH 7.5), a linear concentration gradient of 0-0.2 M sodium chloride in 600 ml of 10 mM Tris-HCl buffer solution (pH 7.5) was prepared to elute the components adsorbed to the column. The degradation activity of egg yolk lecithin was observed in the eluting fraction of 0.05-0.08 M sodium chloride concentration (90 ml). This was used as a crudely purified enzyme fraction.

After 90 ml of the obtained activity fraction were dialyzed 3 times for every 12 hours in 4,000 ml of 20 mM Tris-HCl buffer solution (pH 7.5), the dialysate was added and adsorbed to a MonoQ (Amersham Bioscience K. K.) column (10 mm in diameter×10 cm in length) equilibrated in advance with 20 mM Tris-HCl buffer solution (pH 7.5). After the column was washed sufficiently with 20 mM Tris-HCl buffer solution (pH 7.5), a linear concentration gradient of 0-0.2 M sodium chloride in 250 ml of 20 mM Tris-HCl buffer solution (pH 7.5) was prepared to elute the components adsorbed to the column. The degradation activity of egg yolk lecithin was observed in the eluting fraction of 0.1-0.12 M sodium chloride concentration (25 ml).

After 25 ml of the obtained activity fraction were concentrated, the concentrate was added to a HiLoad Sephadex200pg (Amersham Bioscience K. K.) column (16 mm in diameter×60 cm in length) equilibrated in advance with 10 mM Tris-HCl buffer solution (pH 7.5) containing 0.15 M sodium chloride and eluted with 10 mM Tris-HCl buffer solution (pH 7.5) containing 0.15 M sodium chloride. The degradation activity of egg yolk lecithin was observed in 60-70 ml of the eluting fraction. This fraction was used as a purified enzyme solution.

4) Determination of Molecular Weight of the Purified Enzyme

The molecular weight of the purified enzyme was determined by SDS-PAGE electrophoretic analysis (see Laemmli, U.K., Nature, 227, 680 (1970)) using a 12.5% polyacrylamide gel. The followings were used as standard proteins: a. phosphorylase (MW 94,000), b. albumin (MW 67,000), c. ovalbumin (MW 43,000), d. carbonic anhydrase (MW 30,000), e. trypsin inhibitor (MW 20,100), and f. α-lactalbumin (MW 14,400).

The purified enzyme showed a single band at molecular weight of approximately 87,000.

Example 2

Purification of the Phospholipase C Enzyme(s) from *Aspergillus tamarii* Strain IAM 13907

1) Preparation of a Crude Enzyme Solution

To a 500 ml vol. Erlenmeyer flask (seed flask) containing 100 ml medium of which composition is indicated in Table 2, 1 ml of 5% filter-sterilized sodium deoxycholate solution was added, and *Aspergillus tamarii* strain 13907 was inoculated, and then shaking culture was carried out at 170 rpm and at 26° C. for 5 days. After culture, centrifugation was carried out at 10,000×G and at 4° C. for 10 minutes. The obtained supernatant was used as a crude enzyme solution.

2) Preparation of a Purified Enzyme Solution

A purified enzyme solution was obtained by carrying out purification procedures in the same manner as in Example 1.3).

3) Determination of Molecular Weight of the Purified Enzyme

Molecular weight was determined in the same manner as in Example 1.4).

The purified enzyme showed a single band at molecular weight of approximately 87,000.

Example 3

Purification of the Phospholipase C Enzyme(s) from *Aspergillus oryzaes* Strain NBRC 4190

1) Preparation of a Crude Enzyme Solution

To a 500 ml vol. Erlenmeyer flask (seed flask) containing 100 ml of sterilized medium of which composition is indicated in Table 3, *Aspergillus oryzaes* strain NBRC 4190 was inoculated, and shaking culture was carried out at 170 rpm and at 26° C. for 7 days.

TABLE 3

| Medium | |
|---|---|
| Fish meal | 50 g |

Purified water added to adjust the volume to 1,000 ml.

After culture, centrifugation was carried out at 10,000×G and at 4° C. for 10 minutes. The obtained supernatant was used as a crude enzyme solution.

2) Preparation of a Purified Enzyme Solution 600 ml of the crude enzyme solution obtained in 1) were dialyzed 5 times for every 12 hours in 8,000 ml of 10 mM Tris-HCl buffer solution (pH 7.5). This was added and adsorbed to a DEAE TOYOPEARL (TOSOH CORP.) column (2.2 cm in diameter×20 cm in length) equilibrated in advance with 10 mM Tris-HCl buffer solution (pH 7.5). After the column was washed sufficiently with 10 mM Tris-HCl buffer solution (pH 7.5), a linear concentration gradient of 0-0.6 M sodium chloride in 600 ml of 10 mM Tris-HCl buffer solution (pH 7.5) was prepared to elute the components adsorbed to the column. The degradation activity of egg yolk lecithin was observed in the eluting fraction of 0.30-0.35 M sodium chloride concentration (50 ml). This was used as a crude purified enzyme fraction.

After 50 ml of the obtained activity fraction was dialyzed 3 times for every 12 hours in 4,000 ml of 20 mM Tris-HCl buffer solution (pH 7.5), the dialysate was added and adsorbed to a MonoQ (Amersham Bioscience K. K.) column (10 mm in diameter×10 cm in length) equilibrated in advance with 20 mM Tris-HCl buffer solution (pH 7.5). After the column was washed sufficiently with 20 mM Tris-HCl buffer solution (pH 7.5), a linear concentration gradient of 0-0.6 M sodium chloride in 250 ml of 20 mM Tris-HCl buffer solution (pH 7.5) was prepared to elute the components adsorbed to the column. The degradation activity of egg yolk lecithin was observed in the eluting fraction of 0.12-0.20 M sodium chloride concentration (35 ml).

After 35 ml of the obtained activity fraction were concentrated, the concentrate was added to a HiLoad Sephadex200pg (Amersham Bioscience K. K.) column (16 mm in diameter×60 cm in length) equilibrated in advance with 10 mM Tris-HCl buffer solution (pH 7.5) containing 0.15 M sodium chloride, and was eluted with 10 mM Tris-HCl buffer solution (pH 7.5) containing 0.15 M sodium chloride. The degradation activity of egg yolk lecithin was observed in 60-70 ml of the eluting fraction.

This fraction was used as a purified enzyme solution.

3) Determination of Molecular Weight of the Purified Enzyme

Molecular weight was determined in the same manner as in Example 1.4).

The purified enzyme showed a single band at molecular weight of approximately 87,000.

Example 4

Determination of the Partial Amino Acid Sequence of the Phospholipase C Obtained from *Aspergillus oryzaes* Strain NBRC 4190

The purified enzyme solution was concentrated using an ultrafiltration membrane (VIVASPIN2, Sartorius K.K., molecular weight fraction 10,000) to approximately 1 mg/ml. To 150 µl of the concentrated enzyme solution, 150 µl of denature buffer (6 M guanidine hydrochloride, 10 mM EDTA, and 0.1 M ammonium hydrogencarbonate, pH 7.8) and 6 µl of 50 mM dithiothreitol were added and the reaction was carried out at 95° C. for 10 minutes. After the reaction solution was cooled to room temperature, 30 µl of 50 mM iodoacetamide dissolved in the denature buffer solution was added to the reaction solution, and the reaction was carried out in a dark place at room temperature for 1 hour. This solution was added to a Hitrap Desalting (Amersham Bioscience K. K.) column, equilibrated in advance with 20 mM ammonium hydrogencarbonate (pH 8.0), and eluted with 20 mM ammonium hydrogencarbonate (pH 8.0). The solution eluted in the 1.5-2.5 ml fraction, was freeze-dried and dissolved in 100 µl of 20 mM ammonium hydrogencarbonate (pH 8.0). To the obtained solution, 60 units of trypsin (Modified trypsin, Promega, Inc.) were added, and the enzyme reaction was carried out at 37° C. for 18 hours. The reaction solution was subjected to high performance liquid chromatography (Hitachi, Ltd.) to separate the peaks of the degraded amino acids. Separation conditions are indicated below.

Column: TSKgel™ ODS-120T (4.6 mm×150 mm), TOSOH CORP.
Buffer A: 0.1% TFA/Water
Buffer B: 0.1% TFA/Acetonitrile
Gradient: 10→70% B 2%/ml
Flow: 1 ml/min Among the degraded amino acids separated, 3 peaks (Buffer B concentration: about 30-38%) were isolated, and the amino acid sequences thereof were analyzed by an amino-acid sequence analyzer (Procise cLC, Applied Biosystems Japan Ltd.). The resulting partial amino acid sequences are shown below from their amino termini.

Thr-Ala-Asp-Ser-Ala-Thr-Ala-Ile-Gly-Tyr-Val-Thr-Pro-Ser-Met (SEQ ID NO: 1).
Glu-Ala-Tyr-Gly-Ser-Leu-Leu-Thr-Pro-Pro (SEQ ID NO: 2).
Val-Pro-Pro-Ser-His-Asn-Pro-Gln-Trp-Ala (SEQ ID NO: 3).

Example 5

Identification of DNA Encoding the Phospholipase C Enzyme(s) Derived from *Aspergillus oryaes* Strain NBRC 4190

1) Purification of all RNA

*Aspergillus oryzaes* strain NBRC 4190 was precultured in 20 ml of a liquid medium (2% polypeptone, 0.5% yeast extract, 0.02% dibasic potassium phosphate, and 0.05% magnesium sulfate) at 26° C. for 1 day. Subsequently, 1% of the preculture was inoculated into a liquid medium (5% fish meal) and cultured for 4 days at 26° C. The cultured fungi were collected by aspiration and transferred into a mortar (sterilized by autoclave) that was cooled to −80° C. The fungi were crushed with a pestle, while liquid nitrogen was added, to be powdered. All RNA was purified from the completely powdered fungi using RNeasy Plant Mini Kit (Qiagen, Inc.). 50 µl of 905 ng/µl solution was obtained.

2) Decoding of Phospholipase C Enzyme(s) Gene

The gene sequence was decoded by 5 'RACE and 3' RACE methods. Specifically, PCR was carried out using 5 'RACE System and 3' RACE System (Invitrogen Corporation) and using Ex Taq™ (TAKARA BIO INC.) as a polymerase. The PCR primers used are 5'-GGCCACGCGTCGACTAGTAC-3' and 5'-GACAGTGTAGTCGAGCACAGCGAA-3' for the amplification of the gene sequence from the 5' side, and 5'-GACTCTGCCACCGCAATCGGCTA-3' and 5'-GGC-CACGCGTCGACTAGTAC-3' for the amplification of the gene sequence from the 3' side. The amplification was carried out using PCR cycle: 94° C. for 5 minutes, 30 cycles of (94°

C. for 30 seconds, 55° C. for 30 seconds, and 72° C. for 2 minutes and 30 seconds), and 72° C. for 10 minutes, and then cooling to 4° C. Approximately 1,200 bp or 800 bp DNA fragments were amplified from the 5' or 3' sides of the gene sequence, respectively.

After agarose gel electrophoresis of each PCR product, it was purified using QIAquick™ Gel Extraction Kit (Qiagen, Inc.). The purified product was cloned into a vector using TOPO™ TA cloning kit (Invitrogen Corporation) and transformed. After the transformed *E. coli* was cultured at 37° C. overnight on an agar medium (LB/Agar, Wako Pure Chemical Industries, Ltd.), the formed colonies were cultured at 37° C. overnight in a liquid medium (LB broth, Wako Pure Chemical Industries, Ltd.). Plasmids were purified using QIAprep Spin Miniprep Kit (Qiagen, Inc.) from the grown *E. coli*, and DNA sequence analysis was carried out. The result of the DNA sequence analysis is given in SEQ ID NO: 4. Besides, the amino acid sequence presumed from the DNA sequence is given in SEQ ID NO: 5.

Example 6

Glycopeptidase Treatment of the Phospholipase C Enzyme(s) Derived from *Aspergillus oryzaes* Strain NBRC 4190

1) Enzyme Reaction

The purified enzyme solution was concentrated using an ultrafiltration membrane (VIVASPIN2, Sartorius K.K., molecular weight fraction 10,000). To 20 µl of the concentrated enzyme solution, 15 µl of distilled water, 10 µl of 0.25 mM phosphate buffer solution (pH 7.5) and 2.5 µl of 1 M 2-mercaptoethanol/2% sodium dodecyl sulfate solution were added and the reaction was carried out at 95° C. for 5 minutes. After rapid cooling, 2.5 µl of 15% Triton X-100 (SIGMA-ALDRICH Japan K.K.) were added and then 10 units of glycopeptidase F (SIGMA-ALDRICH Japan K.K.) were added, and the reaction was carried out at 37° C. for 20 hours.

2) Determination of Molecular Weight of Product after Enzyme Reaction

Molecular weight was determined in the same manner as in Example 1.4).

The product after the enzyme reaction showed a single band at molecular weight of approximately 63,000.

Test Example 1

Properties of the Purified Enzyme Solution of the Phospholipase C Enzyme(s) Derived from *Aspergillus oryzae* Strain FERM BP-10200

Activity of the purified enzyme solution obtained in Example 1.3) was measured.

1) pH/Activity

Measurement was carried out according to the method of Example 1.2). However, the enzyme-reaction time was 10 minutes at 37° C. Besides, the following buffer solutions were used: Glycine-hydrochloric acid buffer solution in a case of pH 2.3-3.7; citric acid-sodium citrate buffer solution in a case of pH 3.3-6.2; MOPS buffer solution in a case of pH 6.1-8.0; and Atkins-Pantin buffer solution in a case of pH 8.2-9.2. The hydrolyzing activities of the enzyme at each pH, shown as relative values to 100% of the activity at the pH providing the highest activity, are shown in FIG. 1. The optimum pH in a citrate buffer solution was around pH4.5.

2) Temperature/Activity

Figure 2:
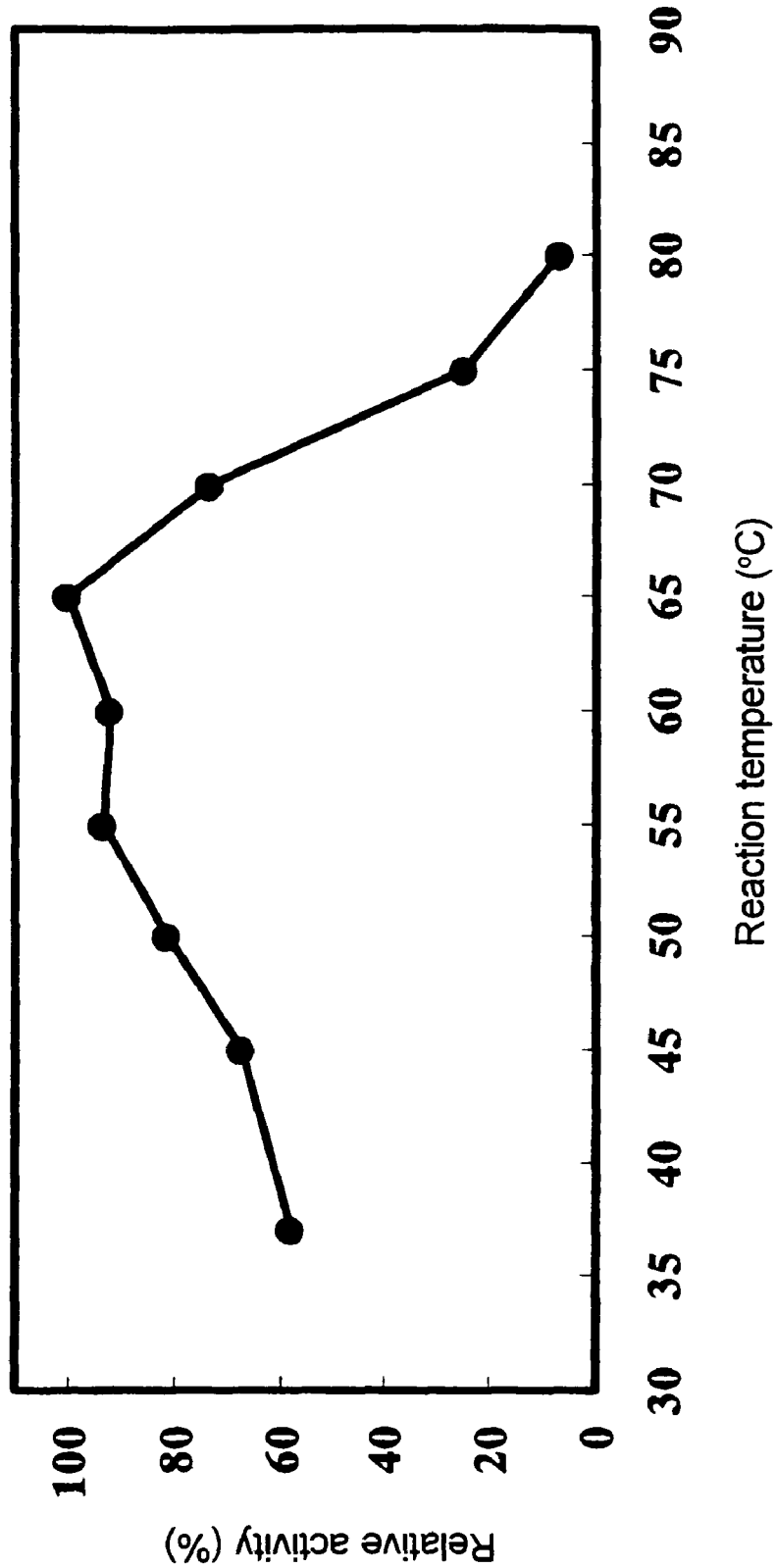
FIG. 2 is a figure showing a relationship between the activity of the purified the phospholipase C enzyme(s) derived from *Aspergillus oryzae* strain FERM BP-10200 and temperature.

The temperature/activity in a citrate buffer solution at pH 4.5 was measured. The measuring method was according to the method in Example 1.2). However, the enzyme-reaction time was 20 minutes at 37° C. The hydrolyzing activities of the enzyme at each temperature, shown as relative values to 100% of the activity at the temperature providing the highest activity, are shown in FIG. 2. The optimal temperature was around 65° C.

3) Temperature/Stability

Figure 3:
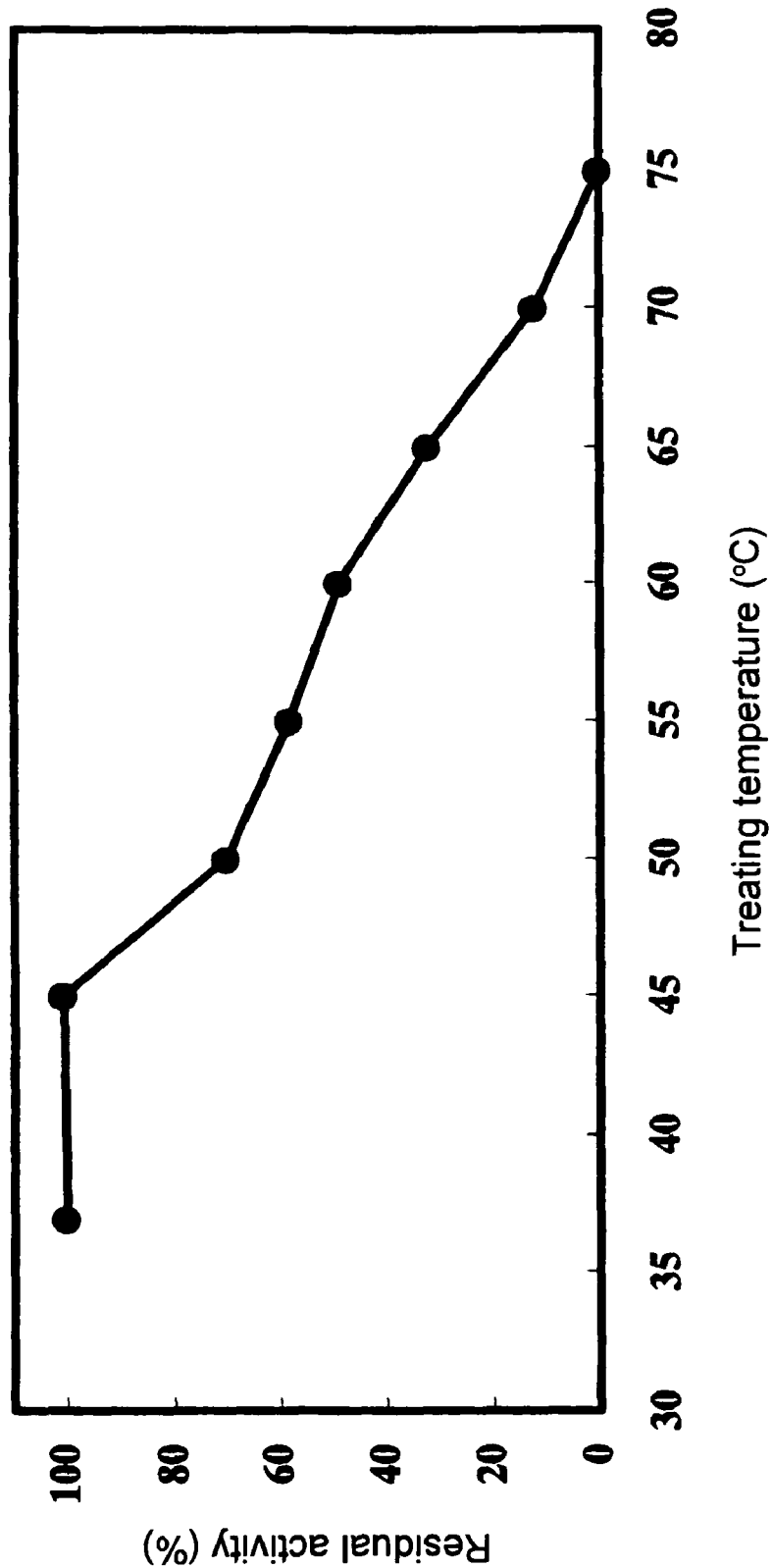
FIG. 3 is a figure showing temperature/stability of the purified phospholipase C enzyme(s) derived from *Aspergillus oryzae* strain FERM BP-10200.

After the purified enzyme solution was treated at various temperatures for 30 minutes, the residual hydrolyzing activity was measured. To 90 µl of 25 mM citrate buffer solution (pH 4.5) maintained in advance at treating temperature, 10 µl of the purified enzyme solution was added and stirred uniformly, and the solution was kept for 30 minutes. To 60 µl of the egg yolk lecithin solution prepared in Example 1, 60 µl of 200 mM citrate buffer solution (pH 4.5) was added and kept at 37° C., and 60 µl of the heat-treated enzyme solution was added and the enzyme reaction was carried out at 37° C. for 30 minutes. The liberated phosphoryl base was quantified according to Example 1.2). The hydrolyzing activities at each temperature, shown as relative values to 100% of the highest residual hydrolyzing activity, are summarized in FIG. 3. The enzyme at pH 4.5 is stable at least at temperature of 60° C. or below.

4) pH/Stability

Figure 4:
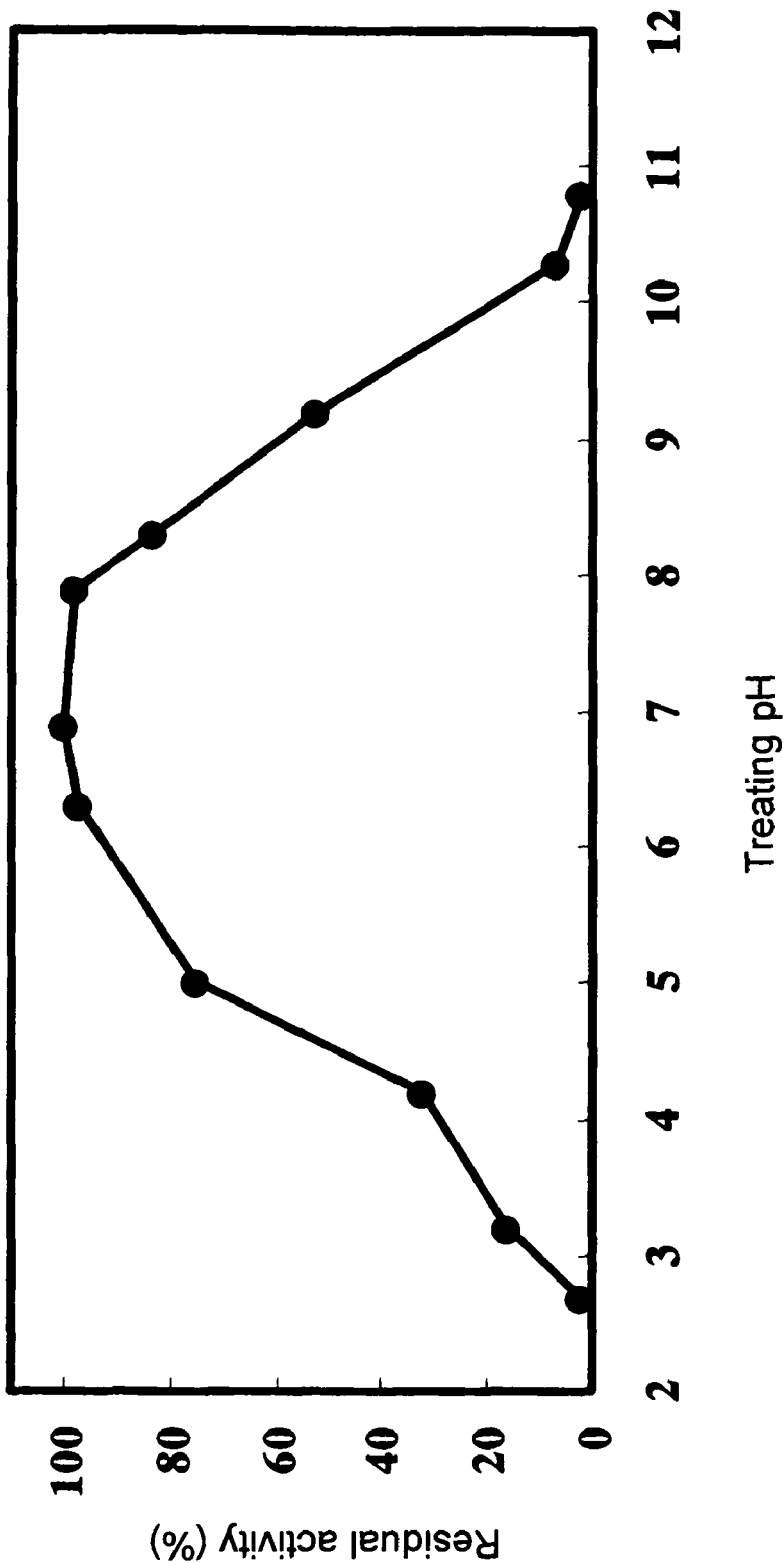
FIG. 4 is a figure showing pH/stability of the purified phospholipase C enzyme(s) derived from *Aspergillus oryzae* strain FERM BP-10200.

To 30 µl of the purified enzyme solution, 30 µl of 200 mM buffer solutions at each pH described below was added and kept at 37° C. for 30 minutes. The following buffer solutions were used: Glycine-hydrochloric acid buffer solution in a case of pH 2.7-3.2; acetic acid-sodium acetate buffer solution in a case of pH 3.5-6.1; MOPS buffer solution in a case of pH 6.3-7.9; and Atkins-Pantin buffer solution in a case of pH 8.3-10.8. To the mixture of 60 µl of 200 mM citrate-buffer-solution (pH 4.5) and 60 µl of the egg yolk lecithin solution in Example 1.2), 60 µl of the solution containing 60 µl of heated enzyme solution added to 60 µl of water was added and stirred uniformly, and the enzyme reaction was carried out at 37° C. for 10 minutes. Liberated phosphoryl base was quantified according to Example 1.2). The hydrolyzing activities at each pH, shown as relative values to 100% of the highest residual hydrolyzing activity, are summarized in FIG. 4. The enzyme was stable at from pH 3 to pH 10.

5) Specific Selectivity of the Purified Enzyme

Subsequently, specific selectivity was measured. The purified enzyme solution prepared in Example 1.3) was used. The measuring method was according to Example 1.2). However, the enzyme reaction was carried out in 200 mM citrate buffer solution (pH 4.5) at 37° C. for 10 minutes. The hydrolyzing activities, shown as relative values to 100% of the hydrolyzing activity in a case of egg yolk phosphatidylcholine, are shown in Table 4.

TABLE 4

| Substrates | Relative activity (%) |
| --- | --- |
| Phosphatidylcholine (egg yolk) | 100 |
| Phosphatidylethanolamine (egg yolk) | 101 |
| Phosphatidylglycerol (egg yolk) | 162 |
| Phosphatidic acid (egg yolk) | 17 |
| Lecithin (egg yolk) | 88 |
| Lysophosphatidylcholine (egg yolk) | 41 |
| Glycerophosphorylcholine (soybean) | 5 |
| p-Nitrophenylphosphate | 0 |
| Phosphatidylcholine (soybean) | 94 |
| Phosphatidylethanolamine (soybean) | 90 |
| Phosphatidylinositol (soybean) | 59 |
| Lecithin (soybean) | 82 |

TABLE 4-continued

| Substrates | Relative activity (%) |
|---|---|
| Sphingomyelin (bovine brain) | 121 |
| Sphingomyelin (egg yolk) | 125 |

Test Example 2

Properties of the Purified Enzyme Solution of the Phospholipase C Enzyme(s) Derived from *Aspergillus tamarii* Strain IAM 13907

Figure 5:
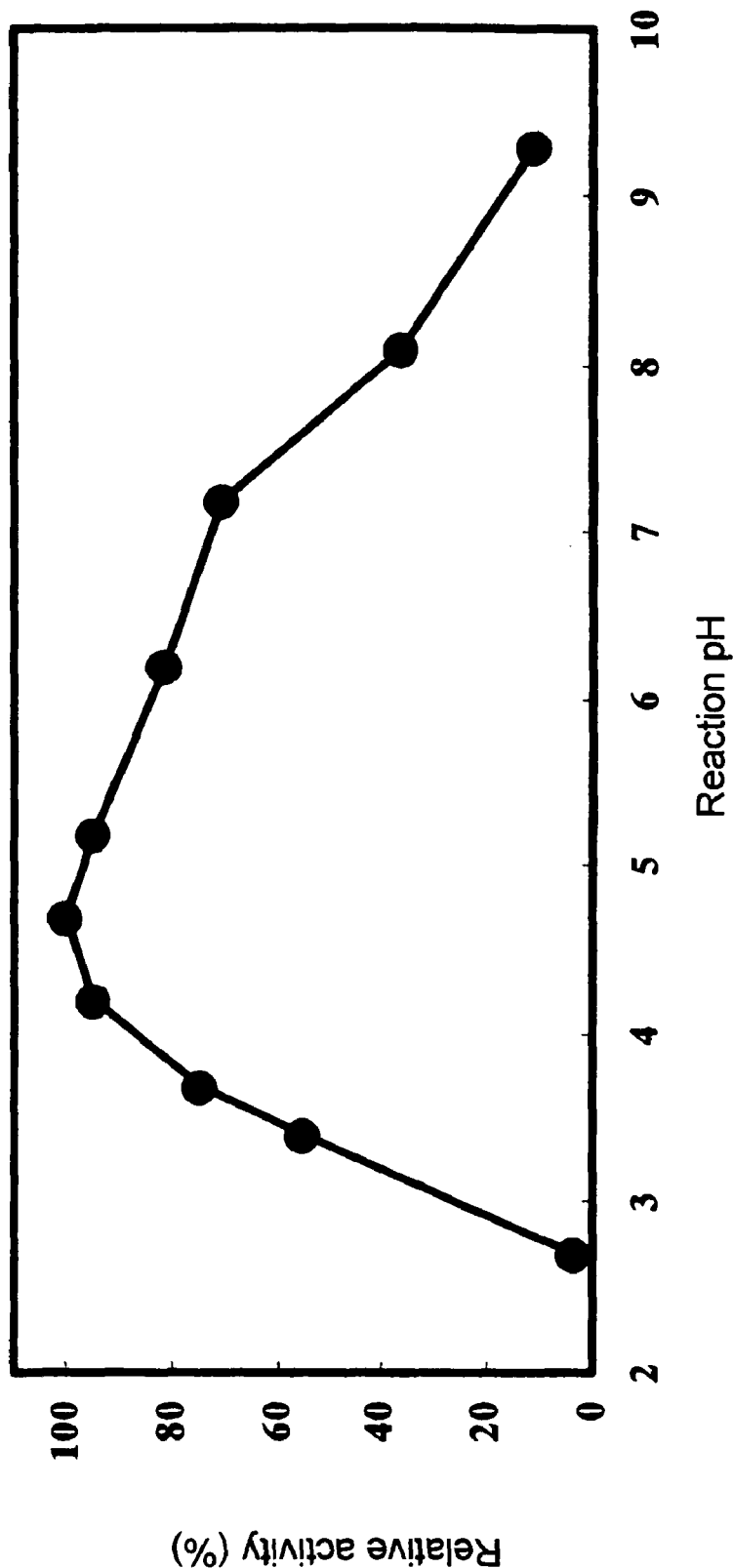
FIG. 5 is a figure showing a relationship between the activity of the purified phospholipase C enzyme(s) derived from *Aspergillus tamarii* strain IAM 13907 and pH.
Figure 6:
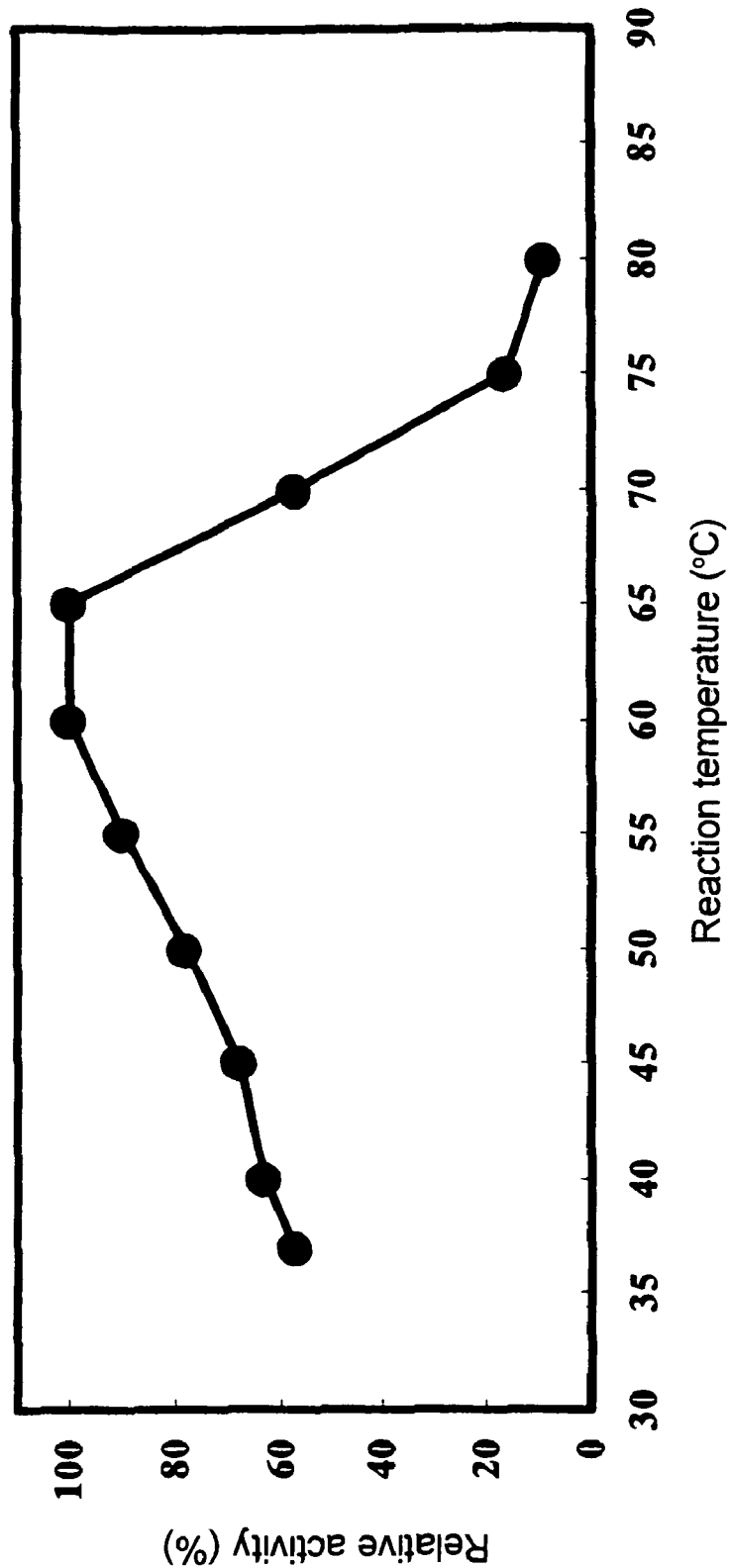
FIG. 6 is a figure showing a relationship between the activity of the purified phospholipase C enzyme(s) derived from *Aspergillus tamarii* strain IAM 13907 and temperature.
Figure 7:
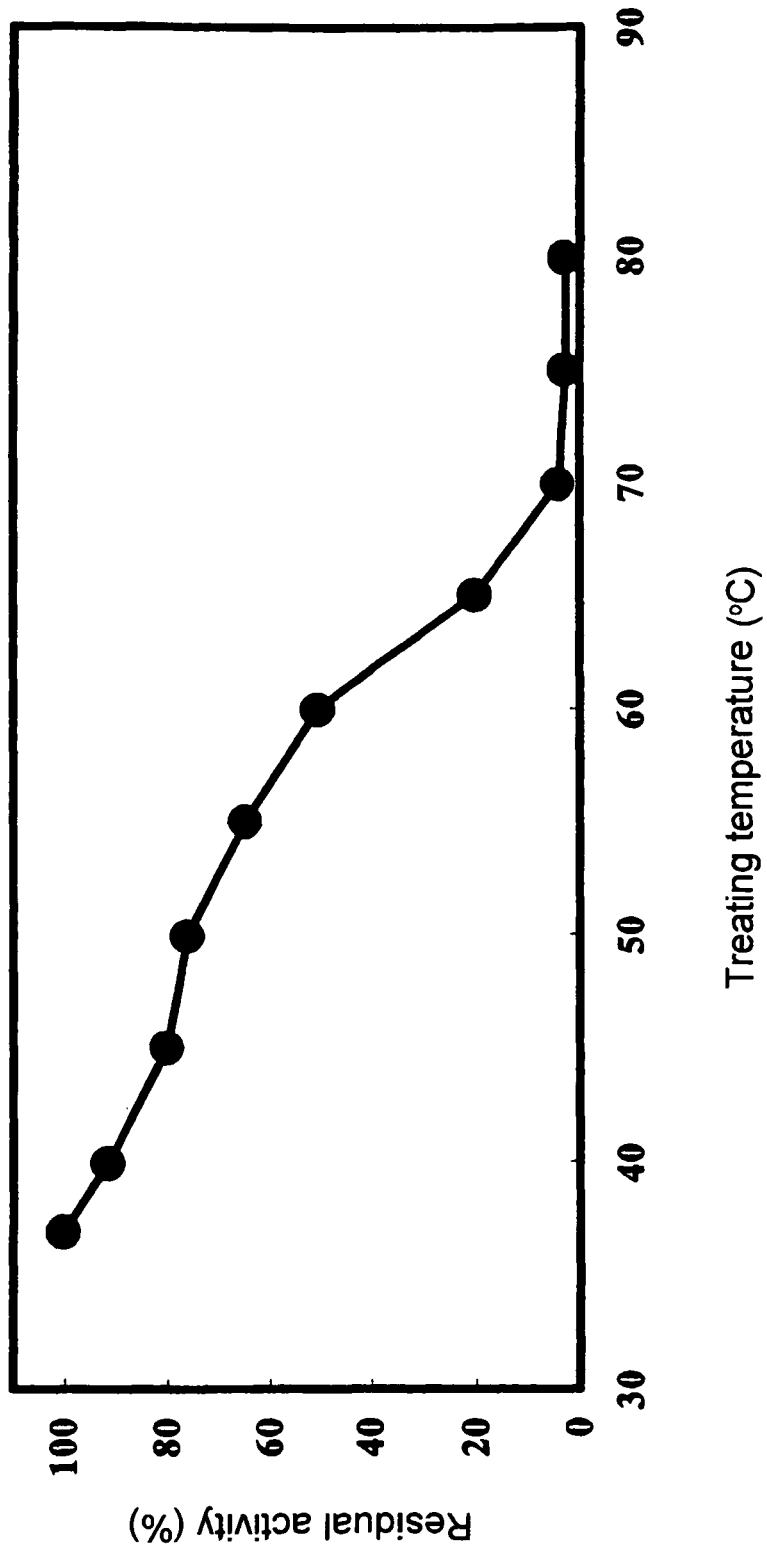
FIG. 7 is a figure showing temperature/stability of the purified phospholipase C enzyme(s) derived from *Aspergillus tamarii* strain IAM 13907.
Figure 8:
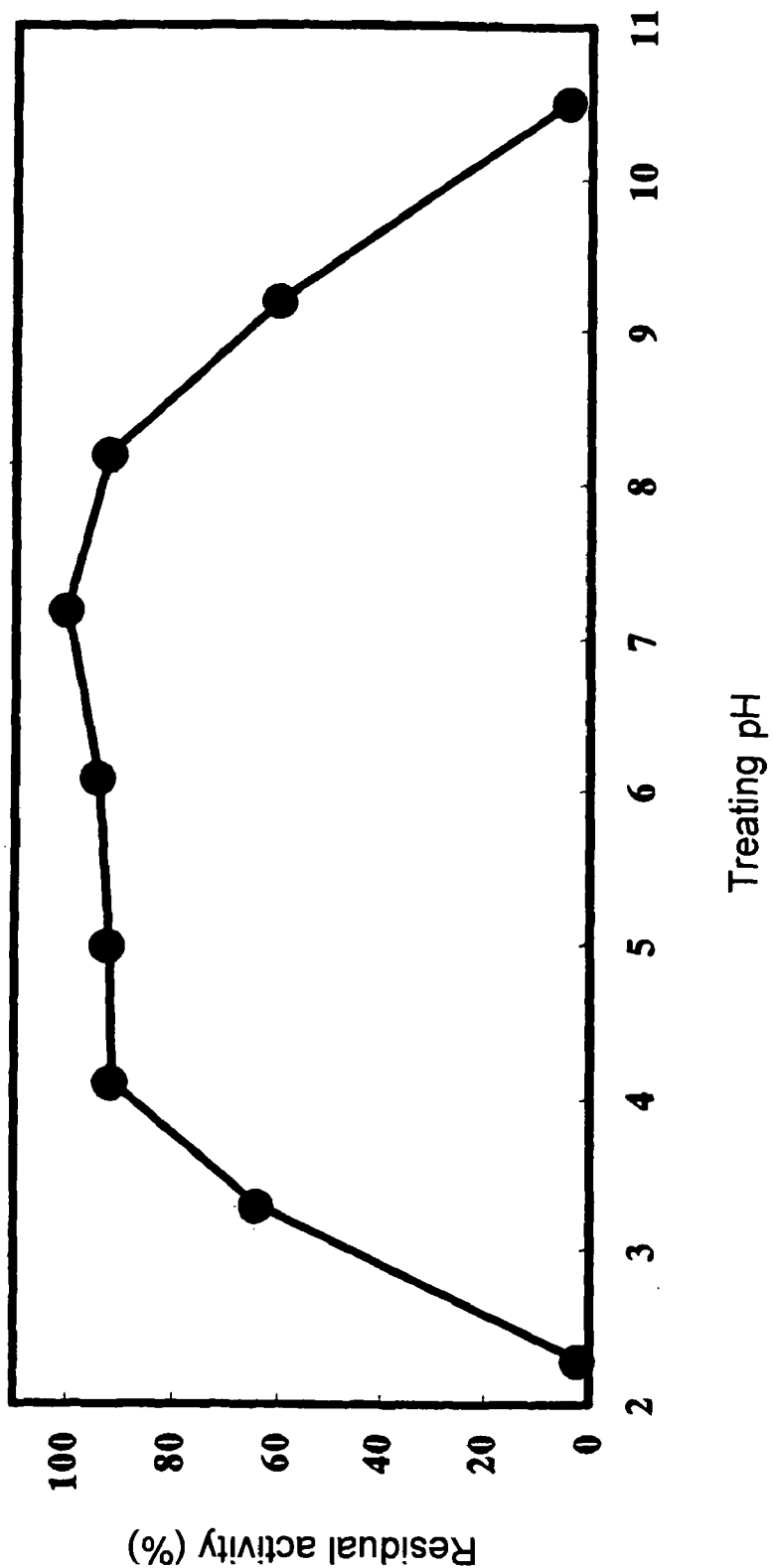
FIG. 8 a figure showing pH/stability of the purified phospholipase C enzyme(s) derived from *Aspergillus tamarii* strain IAM 13907.

Activity of the purified enzyme solution obtained in Example 2.2) was measured.
1) pH/Activity
Measurement was carried out according to the method in Test Example 1. The hydrolyzing activities of the enzyme at each pH, shown as relative values to 100% of hydrolyzing activities under the pH condition providing the highest activity, are shown in FIG. 5. The optimum pH was around pH 4.5.
2) Temperature/Activity
Measurement was carried out according to the method in Test Example 1. The hydrolyzing activities of the enzyme at each temperature, shown as relative values to 100% of hydrolyzing activity under the temperature condition providing the highest activity, are shown in FIG. 6. The optimum temperature was around 65° C.
3) Temperature/Stability
Measurement was carried out according to the method in Test Example 1. The hydrolyzing activity at each temperature, shown as relative values to 100% of residual hydrolyzing activity, are summarized in FIG. 7. The enzyme at pH 4.5 was stable at temperature of 45° C. or below.
4) pH/Stability
Measurement was carried out according to the method in Test Example 1. The hydrolyzing activities at each pH, shown as relative values to 100% of the highest residual hydrolyzing activity, are summarized in FIG. 8. The enzyme was stable at from pH 3 to pH 10.
2) Specific Selectivity of the Purified Enzyme
Measurement was carried out according to the method in Test Example 1. The hydrolyzing activities, shown as relative values to 100% of the hydrolyzing activity in case of egg yolk phosphatidylcholine, are shown in Table 5.

TABLE 5

| Substrates | Relative activity (%) |
|---|---|
| Phosphatidylcholine (egg yolk) | 100 |
| Phosphatidylethanolamine (egg yolk) | 94 |
| Phosphatidylglycerol (egg yolk) | 191 |
| Phosphatidic acid (egg yolk) | 16 |
| Lecithin (egg yolk) | 91 |
| Lysophosphatidylcholine (egg yolk) | 53 |

TABLE 5-continued

| Substrates | Relative activity (%) |
|---|---|
| Glycerophosphorylcholine (soybean) | 8 |
| p-Nitrophenylphosphate | 2 |
| Phosphatidylcholine (soybean) | 91 |
| Phosphatidylethanolamine (soybean) | 84 |
| Phosphatidylinositol (soybean) | 57 |
| Lecithin (soybean) | 75 |

Test Example 3

Properties of the Purified Enzyme Solution of the Phospholipase C Enzyme(s) Derived from *Aspergillus oryzaes* Strain NBRC 4190

Figure 9:
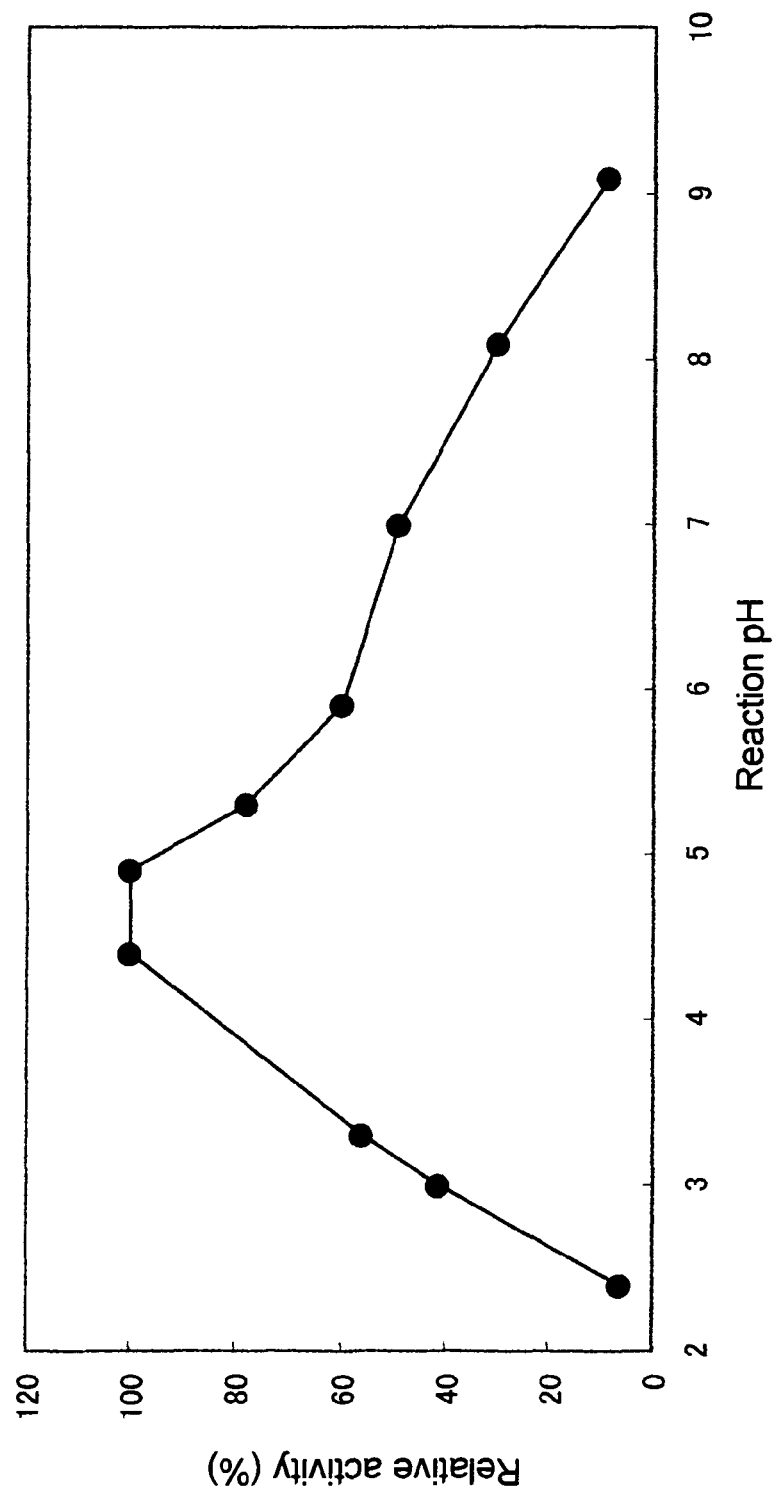
FIG. 9 is a figure showing a relationship between the activity of the purified phospholipase C enzyme(s) derived from *Aspergillus oryzae* strain NBRC 4190 and pH.

Activity of the purified enzyme solution obtained in Example 3.2) was measured.
1) pH/Activity
Measurement carried out according to the method in Test Example 1. The hydrolyzing activities of the enzyme at each pH, shown as relative values to 100% of hydrolyzing activity under the pH condition providing the highest activity, are shown in FIG. 9. The optimum pH was around pH 4.5.
2) Specific Selectivity of the Purified Enzyme
Measurement carried out according to the method in Test Example 1. The hydrolyzing activities, shown as relative values to 100% of the hydrolyzing activity in a case of egg yolk phosphatidylcholine, are shown in Table 6.

TABLE 6

| Substrates | Relative activity (%) |
|---|---|
| Phosphatidylcholine (egg yolk) | 100 |
| Phosphatidylethanolamine (egg yolk) | 111 |
| Phosphatidylglycerol (egg yolk) | 201 |
| Phosphatidic acid (egg yolk) | 22 |
| Lecithin (egg yolk) | 89 |
| Lysophosphatidylcholine (egg yolk) | 46 |
| Glycerophosphorylcholine (soybean) | 3 |
| p-Nitrophenylphosphate | 1 |
| Phosphatidylcholine (soybean) | 97 |
| Phosphatidylethanolamine (soybean) | 99 |
| Phosphatidylinositol (soybean) | 61 |
| Lecithin (soybean) | 81 |

EFFECTS OF THE INVENTION

As described above, the phospholipase C enzyme(s) of the present invention is an enzyme(s) derived from *Aspergillus oryzae* strain FERM BP-10200 or strain NBRC 4190, or *Aspergillus tamarii* strain IAM 13907 and has excellent safety, ability to hydrolyze efficiently various glycerophospholipids at both acidic range and around neutral range and the activity also in a citrate buffer solution as well as having some degree of heat stability and not hydrolyzing any phosphate esters except for phospholipids; and has excellent effects in both food and oil mills industry fields.

The invention claimed is:

1. An isolated DNA consisting of the nucleotide sequence of SEQ ID NO: 4, wherein said isolated DNA encodes a phospholipase C enzyme.

2. An isolated DNA that encodes a phospholipase C enzyme, wherein said isolated DNA comprises the nucleotide sequence of SEQ ID NO: 4.

3. The isolated DNA of claim 1, wherein the DNA encodes a protein consisting of the amino acid sequence of SEQ ID NO: 5.

* * * * *